US012426968B2

(12) United States Patent
Kobayashi et al.

(10) Patent No.: US 12,426,968 B2
(45) Date of Patent: Sep. 30, 2025

(54) ROBOTIC SURGICAL SYSTEM AND METHOD FOR SETTING PIVOT POSITION

(71) Applicant: KAWASAKI JUKOGYO KABUSHIKI KAISHA, Kobe (JP)

(72) Inventors: Ayataka Kobayashi, Kobe (JP); Tsuyoshi Tojo, Kobe (JP); Hirofumi Yamamori, Kobe (JP); Jota Ida, Kobe (JP); Hiroaki Kitatsuji, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 480 days.

(21) Appl. No.: 17/872,077

(22) Filed: Jul. 25, 2022

(65) Prior Publication Data

US 2023/0032548 A1 Feb. 2, 2023

(30) Foreign Application Priority Data

Jul. 27, 2021 (JP) .................................. 2021-122348

(51) Int. Cl.
*A61B 34/10* (2016.01)
*A61B 34/00* (2016.01)
*A61B 34/30* (2016.01)
*A61B 34/35* (2016.01)

(52) U.S. Cl.
CPC .............. *A61B 34/35* (2016.02); *A61B 34/25* (2016.02); *A61B 34/30* (2016.02); *A61B 2034/105* (2016.02); *A61B 2034/256* (2016.02); *A61B 2034/301* (2016.02)

(58) Field of Classification Search
CPC ......... A61B 34/35; A61B 34/25; A61B 34/30; A61B 2034/105; A61B 2034/256; A61B 2034/301; A61B 17/34; A61B 2034/2059; A61B 2090/3612
See application file for complete search history.

(56) References Cited

U.S. PATENT DOCUMENTS

| 12,357,402 | B2 | 7/2025 | Kanazawa et al. | |
| 2007/0118034 | A1* | 5/2007 | Mark | A61B 90/39 600/431 |
| 2011/0234484 | A1* | 9/2011 | Ogawa | A61B 1/00042 345/204 |
| 2015/0202015 | A1 | 7/2015 | Elhawary et al. | |
| 2016/0100898 | A1* | 4/2016 | Jinno | A61B 34/37 606/130 |
| 2017/0196644 | A1 | 7/2017 | Elhawary et al. | |
| 2018/0200013 | A1 | 7/2018 | Elhawary et al. | |
| 2018/0271602 | A1* | 9/2018 | Frey | A61F 2/30942 |
| 2019/0133704 | A1 | 5/2019 | Hiratsuka et al. | |
| 2020/0113635 | A1 | 4/2020 | Ida et al. | |

(Continued)

FOREIGN PATENT DOCUMENTS

| JP | 2015-524309 A | 8/2015 |
| JP | 2017-189495 A | 10/2017 |

(Continued)

*Primary Examiner* — Harry Y Oh
(74) *Attorney, Agent, or Firm* — METROLEX IP LAW GROUP, PLLC; Robert L. Scott, Esq.

(57) ABSTRACT

In a robotic surgical system, a controller is configured or programmed to set a temporary pivot position based on an operation on a pivot position setter and store a position adjusted by a predetermined length from the temporary pivot position as a pivot position in a storage.

20 Claims, 15 Drawing Sheets

(56) References Cited

U.S. PATENT DOCUMENTS

2020/0315721 A1   10/2020  Rabindran et al.
2021/0330409 A1*  10/2021  Kitatsuji ................ A61B 34/37
2022/0378518 A1*  12/2022  Kanazawa ............. A61B 34/30

FOREIGN PATENT DOCUMENTS

JP        2020-058672 A    4/2020
JP           6839874 B1    3/2021

* cited by examiner

ROBOTIC SURGICAL SYSTEM AND METHOD FOR SETTING PIVOT POSITION

CROSS-REFERENCE TO RELATED APPLICATION

The present application claims priority to JP2021-122348, which is incorporated herein by reference.

BACKGROUND OF THE INVENTION

Field of the Invention

The present disclosure relates to a robotic surgical system and a method for setting a pivot position.

Description of the Background Art

Conventionally, a surgical robot that moves a surgical instrument attached to a manipulator arm with a pivot position as a fulcrum is known. Japanese Translation of PCT International Application Publication No 2015-524309 discloses a robotic surgical system including a robot, an end effector, a surgical instrument held by the end effector, and a robot controller. In this robotic surgical system, the surgical instrument is inserted into the patient's body through a small opening formed in the patient. Then, the robot is controlled by the robot controller to rotate the surgical instrument about a predetermined fulcrum.

In Japanese Translation of PCT International Application Publication No 2015-524309, a potentiometer is attached to the end effector of the robot. After the potentiometer is attached to the end effector of the robot, a cable of the potentiometer is extended along the surgical instrument. The cable is extended to the patient's opening into which the surgical instrument is inserted. A distance between the end effector and the patient's opening is detected by the potentiometer. The robot controller sets the fulcrum of rotation of the surgical instrument based on the detected distance.

In Japanese Translation of PCT International Application Publication No 2015-524309, the cable of the potentiometer is extended to the patient's opening, and thus the potentiometer measures a distance between the end effector and the body surface of the patient. In this case, the fulcrum of rotation of the surgical instrument is set on the body surface of the patient. It is desirable that the abdominal wall of the patient have a thickness and the influence of rotation of the surgical instrument on the patient be small. Thus, it is desirable that the center of rotation of the surgical instrument be set closer to the center of the abdominal wall than the body surface of the patient. Therefore, it is desired to set a pivot position, which is the fulcrum of rotation of the surgical instrument, to an appropriate position.

SUMMARY OF THE INVENTION

The present disclosure is intended to solve the above problems. The present disclosure aims to provide a robotic surgical system and a method for setting a pivot position each capable of setting a pivot position to an appropriate position.

In order to attain the aforementioned object, a robotic surgical system according to a first aspect of the present disclosure includes a manipulator arm having a tip end to which a surgical instrument is attached, a pivot position setter to set a pivot position that serves as a fulcrum for movement of the surgical instrument attached to the manipulator arm, a storage, and a controller. The controller is configured or programmed to set a temporary pivot position based on an operation on the pivot position setter, and store a position adjusted by a predetermined length from the temporary pivot position as the pivot position in the storage.

In the robotic surgical system according to the first aspect of the present disclosure, as described above, the controller is configured or programmed to set the temporary pivot position based on the operation on the pivot position setter and store the position adjusted by the predetermined length from the temporary pivot position as the pivot position in the storage. Accordingly, the position adjusted by the predetermined length from the temporary pivot position set on the body surface of a patient can be used as the pivot position. For example, the pivot position can be set closer to the center of the abdominal wall than the body surface of the patient. Therefore, the pivot position can be appropriately set.

A method for setting a pivot position according to a second aspect of the present disclosure includes receiving an operation on a pivot position setter to set a pivot position that serves as a fulcrum for movement of a surgical instrument attached to a manipulator arm, setting a temporary pivot position based on the operation on the pivot position setter, and storing a position adjusted by a predetermined length from the set temporary pivot position as the pivot position in a storage.

As described above, the method for setting the pivot position according to the second aspect of the present disclosure includes setting the temporary pivot position based on the operation on the pivot position setter and storing the position adjusted by the predetermined length from the set temporary pivot position as the pivot position in the storage. Accordingly, the position adjusted by the predetermined length from the temporary pivot position set on the body surface of a patient can be used as the pivot position. For example, the pivot position can be set closer to the center of the abdominal wall than the body surface of the patient. Therefore, it is possible to provide the method for setting the pivot position capable of setting the pivot position to an appropriate position.

According to the present disclosure, as described above, the pivot position can be set to the appropriate position.

The foregoing and other objects, features, aspects and advantages of the present disclosure will become more apparent from the following detailed description of the present disclosure when taken in conjunction with the accompanying drawings.

DESCRIPTION OF THE PREFERRED EMBODIMENTS

Figure 1:
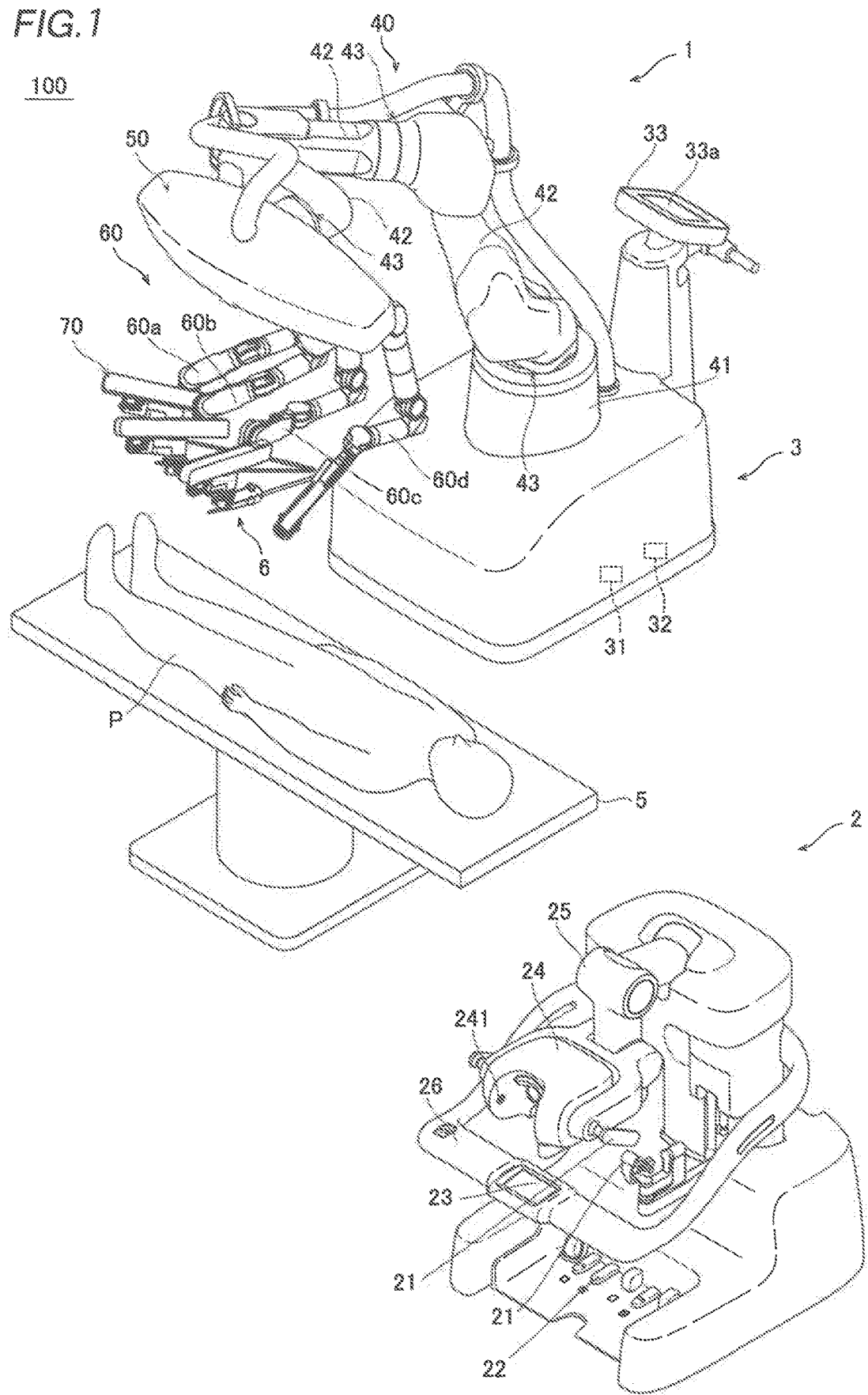
FIG. 1 is a diagram showing the configuration of a surgical system according to a first embodiment.

Embodiments of the present disclosure are hereinafter described with reference to the drawings.

First Embodiment

The configuration of a surgical system 100 according to a first embodiment is now described with reference to FIGS. 1 to 18. The surgical system 100 includes a medical manipulator 1 that is a patient P-side apparatus and a remote control apparatus 2 that is an operator-side apparatus to operate the medical manipulator 1. The medical manipulator 1 includes a medical cart 3, and is movable. The remote control apparatus 2 is spaced apart from the medical manipulator 1, and the medical manipulator 1 is remotely operated by the remote control apparatus 2. An operator (such as a doctor) inputs a command to the remote control apparatus 2 to cause the medical manipulator 1 to perform a desired operation. The remote control apparatus 2 transmits the input command to the medical manipulator 1. The medical manipulator 1 operates based on the received command. The medical manipulator 1 is arranged in an operating room that is a sterilized sterile field. The medical manipulator 1 is an example of a robotic surgical system.

The remote control apparatus 2 is arranged inside or outside the operating room, for example. The remote control apparatus 2 includes operation arms 21, operation pedals 22, a touch panel 23, a monitor 24, a support arm 25, and a support bar 26. The operation arms 21 define operation handles for the operator to input commands. The monitor 24 is a scope-type display that displays an image captured by an endoscope 6. The support arm 25 supports the monitor 24 so as to align the height of the monitor 24 with the height of the face of the operator. The touch panel 23 is arranged on the support bar 26. The operator's head is detected by a sensor provided in the vicinity of the monitor 24 such that the medical manipulator 1 can be operated by the remote control apparatus 2. The operator operates the operation arms 21 and the operation pedals 22 while visually recognizing an affected area on the monitor 24. Thus, a command is input to the remote control apparatus 2. The command input to the remote control apparatus 2 is transmitted to the medical manipulator 1. The operation arms 21 are examples of an operation handle. The touch panel 23 is an example of an input or a receiver.

The medical cart 3 includes a controller 31 that controls the operation of the medical manipulator 1 and a storage 32 that stores programs or the like to control the operation of the medical manipulator 1. The controller 31 of the medical cart 3 controls the operation of the medical manipulator 1 based on the command input to the remote control apparatus 2.

The medical cart 3 includes an input 33. The input 33 receives operations to move a positioner 40, an arm base 50, and a plurality of manipulator arms 60 or change their postures mainly in order to prepare for surgery before the surgery.

Figure 2:
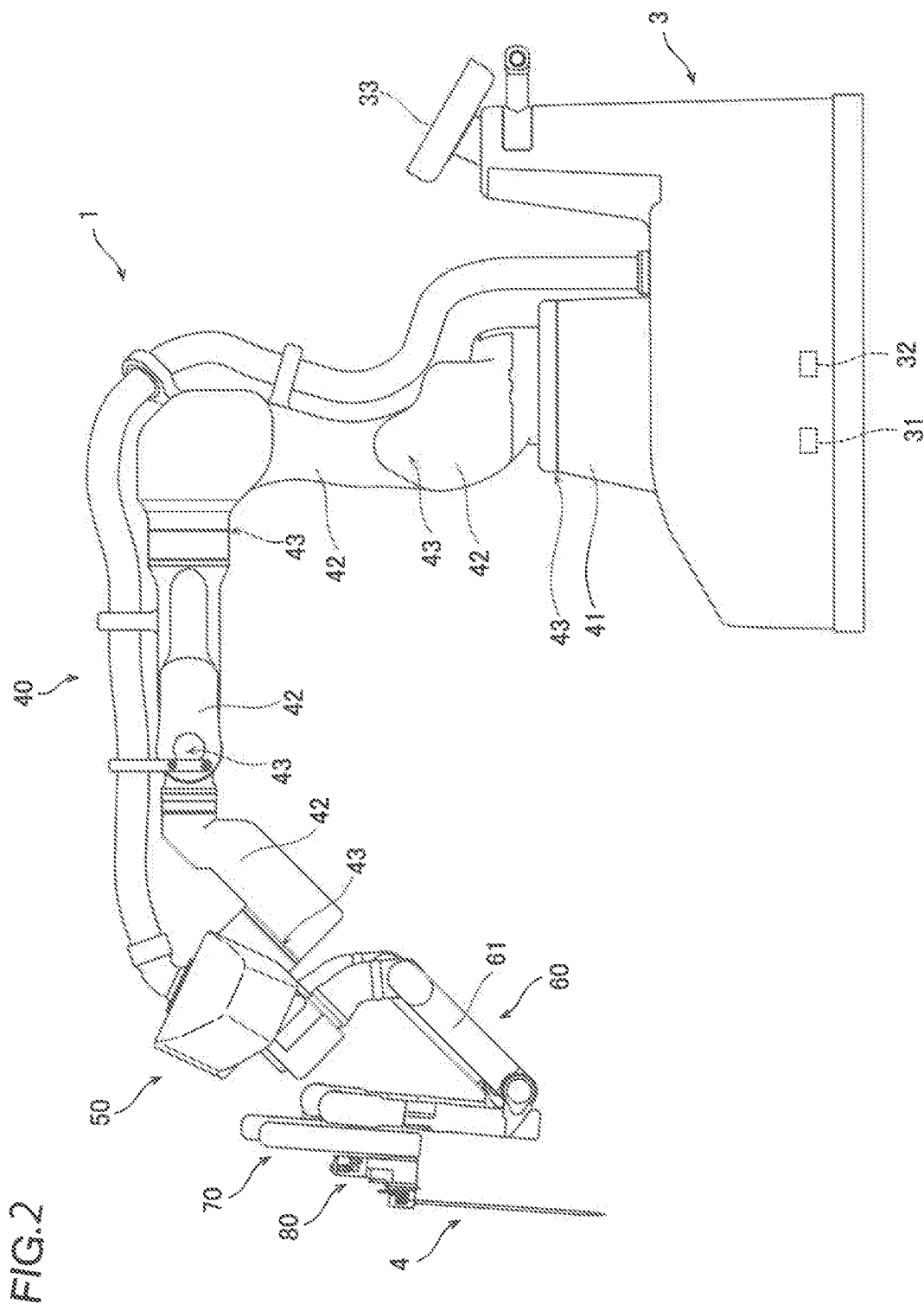
FIG. 2 is a diagram showing the configuration of a medical manipulator according to the first embodiment.

The medical manipulator 1 shown in FIGS. 1 and 2 is arranged in the operating room. The medical manipulator 1 includes the medical cart 3, the positioner 40, the arm base 50, and the plurality of manipulator arms 60. The arm base 50 is attached to the tip end of the positioner 40. The arm base 50 has a relatively long rod shape. The bases of the plurality of manipulator arms 60 are attached to the arm base 50. Each of the plurality of manipulator arms 60 is able to take a folded and stored posture. The arm base 50 and the plurality of manipulator arms 60 are covered with sterile drapes and used.

The positioner 40 includes a 7-axis articulated robot, for example. The positioner 40 is arranged on the medical cart 3. The positioner 40 moves the arm base 50. Specifically, the positioner 40 moves the position of the arm base 50 three-dimensionally.

The positioner 40 includes a base 41 and a plurality of links 42 coupled to the base 41. The plurality of links 42 are coupled to each other by joints 43.

As shown in FIG. 2, a surgical instrument 4 is attached to the tip end of each of the plurality of manipulator arms 60. The surgical instrument 4 includes a replaceable instrument or the endoscope 6 shown in FIG. 7, for example.

Figure 3:
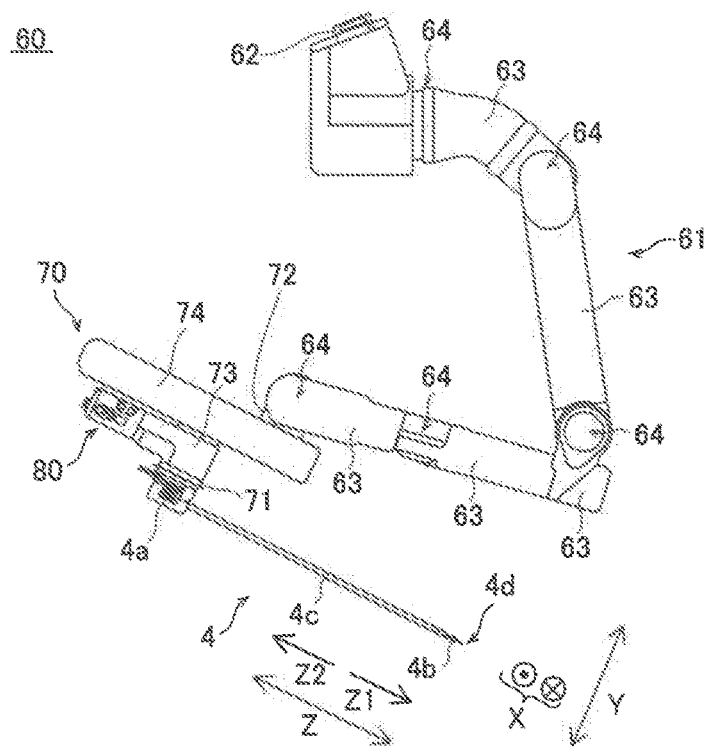
FIG. 3 is a diagram showing the configuration of an arm of the medical manipulator according to the first embodiment.

As shown in FIG. 3, the instrument as the surgical instrument 4 includes a driven unit 4*a* driven by servomotors M2 provided in a holder 71 of each of the manipulator arms 60. An end effector 4*b* is provided at the tip end of the instrument. The end effector 4*b* includes a pair of forceps, a pair of scissors, a grasper, a needle holder, a microdissector, a stable applier, a tacker, a suction cleaning tool, a snare wire, a clip applier, etc. as instruments having joints. The end effector 4*b* includes a cutting blade, a cautery probe, a washer, a catheter, a suction orifice, etc. as instruments having no joint. The surgical instrument 4 includes a shaft 4*c* that connects the driven unit 4*a* to the end effector 4*b*. The driven unit 4*a*, the shaft 4*c*, and the end effector 4*b* are arranged along a Z direction.

The configuration of the manipulator arms 60 is now described in detail. As shown in FIG. 3, each of the manipulator arms 60 includes an arm portion 61 and a translation mechanism 70 provided at the tip end of the arm portion 61. The arm portion 61 includes a base 62, links 63, and joints 64. The manipulator arms 60 three-dimensionally move the tip end sides with respect to the arm base 50 on the base sides of the manipulator arms 60. The plurality of manipulator arms 60 have the same or similar configuration as each other.

Figure 13:
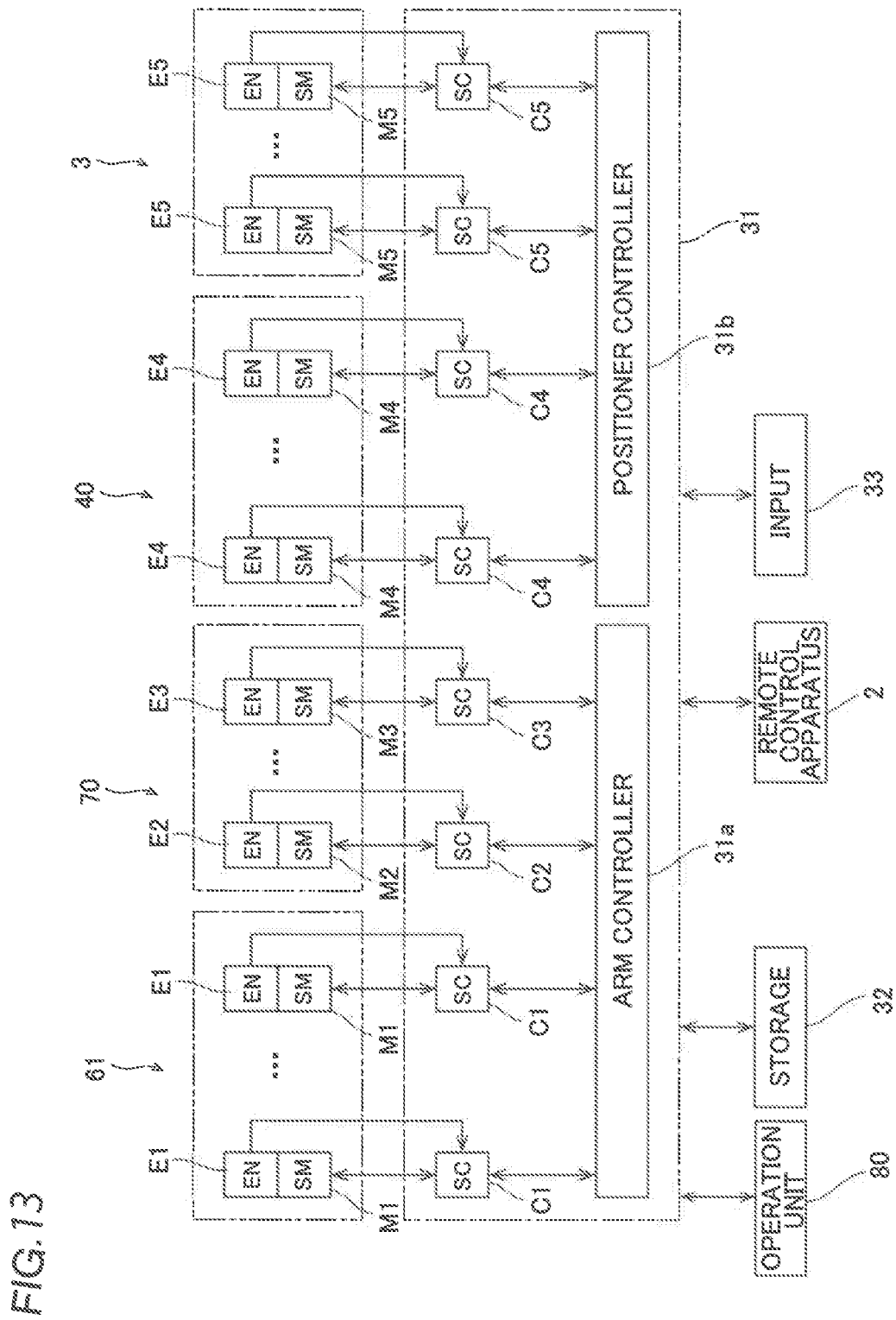
FIG. 13 is a block diagram showing the configuration of a controller of the medical manipulator.

The translation mechanism 70 is provided at the tip end of the arm portion 61, and the surgical instrument 4 is attached thereto. The translation mechanism 70 translates the surgical instrument 4 in a direction in which the surgical instrument 4 is inserted into a patient P. Furthermore, the translation mechanism 70 translates the surgical instrument 4 relative to the arm portion 61. Specifically, the translation mechanism 70 includes the holder 71 that holds the surgical instrument 4. The servomotors M2 shown in FIG. 13 are housed in the holder 71. The servomotors M2 rotate rotary bodies provided in the driven unit 4a of the surgical instrument 4. The rotary bodies of the driven unit 4a are rotated such that the end effector 4b is operated.

The manipulator arms 60 are attachable to and detachable from the arm base 50. The arm portion 61 and the translation mechanism 70 do not include a mechanism or an instrument to hold a trocar T. Consequently, a space in the vicinity of the body surface S of the patient P in which a plurality of trocars T are arranged is widened, and it becomes possible to easily perform an operation in the vicinity of the body surface S of the patient P in which the plurality of trocars T are arranged.

The arm portion 61 includes a 7-axis articulated robot arm. The arm portion 61 includes the base 62 to attach the arm portion 61 to the arm base 50, and a plurality of links 63 coupled to the base 62. The plurality of links 63 are coupled to each other by the joints 64.

The translation mechanism 70 translates the surgical instrument 4 attached to the holder 71 along the Z direction, which is a direction in which the shaft 4c extends, by translating the holder 71 along the Z direction. Specifically, the translation mechanism 70 includes a base end side link 72 connected to the tip end of the arm portion 61, a tip end side link 73, and a coupling link 74 provided between the base end side link 72 and the tip end side link 73. The holder 71 is provided on the tip end side link 73.

The coupling link 74 of the translation mechanism 70 is configured as a double speed mechanism that moves the tip end side link 73 relative to the base end side link 72 along the Z direction. The tip end side link 73 is moved along the Z direction relative to the base end side link 72 such that the surgical instrument 4 provided on the holder 71 is translated along the Z direction. The tip end of the arm portion 61 is connected to the base end side link 72 so as to rotate the base end side link 72 about a Y direction orthogonal to the Z direction.

Figure 4:
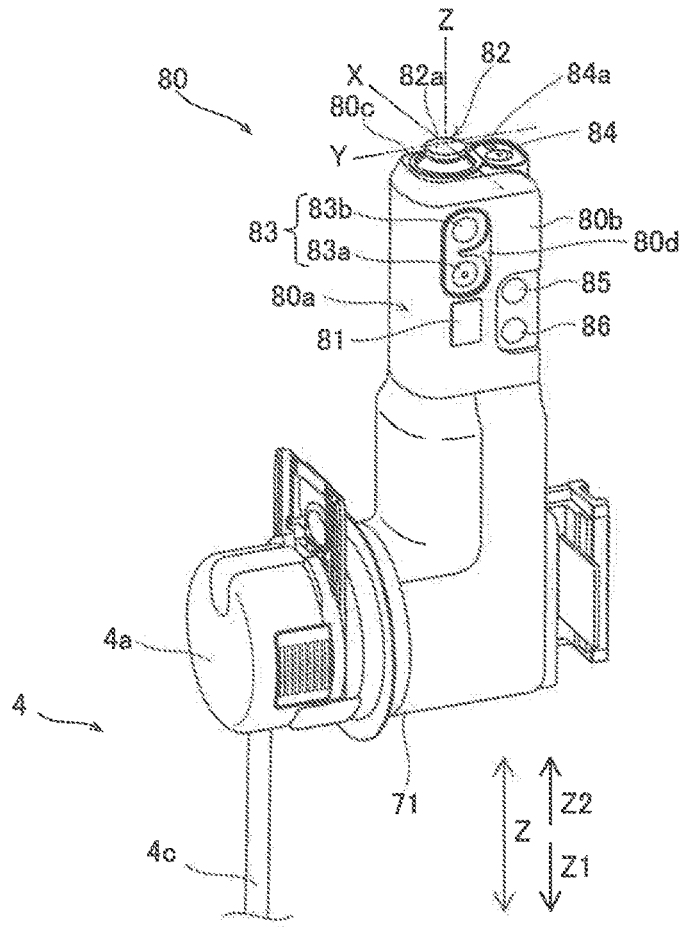
FIG. 4 is a perspective view showing the configuration of an operation unit of the medical manipulator according to the first embodiment.

As shown in FIG. 4, the medical manipulator 1 includes an operation unit 80 attached to each of the manipulator arms 60 to operate the manipulator arm 60. The operation unit 80 includes enable switches 81, a joystick 82, and switch units 83. The enable switches 81 enable or disable movement of the manipulator arm 60 in response to the joystick 82 and the switch units 83. The enable switches 81 enable movement of the surgical instrument 4 by the manipulator arm 60 when the enable switches 81 are pressed by an operator (such as a nurse or an assistant) grasping the operation unit 80.

Specifically, the enable switches 81 are push-button switches that are pressed by the operator's fingers. The enable switches 81 are pressed such that it becomes possible to perform a control to energize servomotors M1 to M3. In other words, the enable switches 81 are pressed such that it becomes possible to perform a control to drive the servomotors M1 to M3. That is, it is possible to perform a control to move the manipulator arm 60 only while the enable switches 81 are being pressed.

Figure 6:
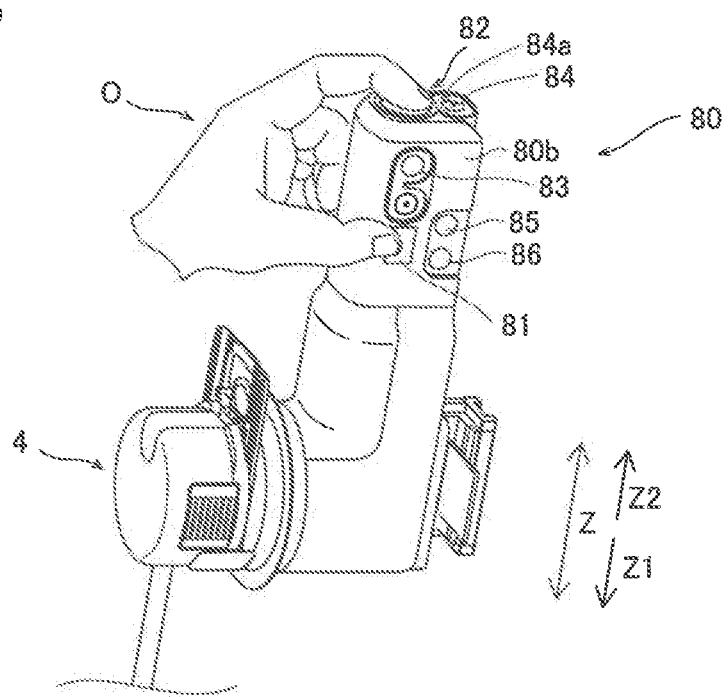
FIG. 6 is a diagram showing a state in which an operator grasps the operation unit of the medical manipulator according to the first embodiment.

As shown in FIG. 6, the operator tilts and operates the joystick 82 with their finger. The manipulator arm 60 is controlled to move while changing its moving direction and moving speed according to a direction in which the joystick 82 is tilted and an angle at which the joystick 82 is tilted. The operator brings their finger into contact with the tip end 82a of the joystick 82, moves their finger, and tilts the joystick 82 to operate the joystick 82. Only while the enable switches 81 are being pressed, a signal input based on an operation on the joystick 82 is received. That is, while the enable switches 81 are not pressed, the manipulator arm 60 is not moved even when the joystick 82 is operated.

Figure 5:
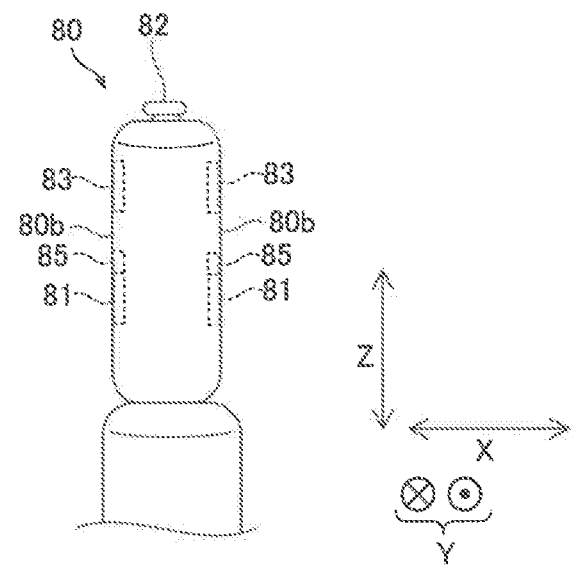
FIG. 5 is a side view showing the configuration of the operation unit of the medical manipulator according to the first embodiment.

The enable switches 81 are provided on the outer peripheral surface 80a of the operation unit 80, and when the operator grasps the outer peripheral surface 80a of the operation unit 80 and presses the enable switches 81, movement of the surgical instrument 4 by the manipulator arm 6 is enabled. As shown in FIG. 5, a pair of enable switches 81 are provided on opposite sides of the outer peripheral surface 80a of the operation unit 80. The enable switches 81 are provided on opposite sides of the outer peripheral surface 80a of the operation unit 80 on which the switch units 83 are provided. Specifically, the cross-section of the operation unit 80 has a substantially rectangular shape, and the enable switches 81 and the switch units 83 are provided on surfaces 80b of the operation unit 80 that face each other. More specifically, the operation unit 80 has a substantially prismatic shape, and the enable switches 81 and the switch units 83 are provided on the surfaces 80b along the longitudinal direction of the substantially prismatic operation unit 80. When the operator grasps the outer peripheral surface 80a of the operation unit 80 and presses at least one of the enable switches 81 provided on the opposite sides of the outer peripheral surface 80a of the operation unit 80, movement of the manipulator arm 60 is enabled.

Only one of the enable switches 81 provided on the opposite sides of the outer peripheral surface 80a of the operation unit 80 needs to be pressed to enable movement of the manipulator arm 60. Thus, it is not necessary to press both of the enable switches 81 provided on the opposite sides of the outer peripheral surface 80a of the operation unit 80, and thus the burden on the operator can be reduced while the convenience of the operator is improved.

As shown in FIG. 4, the joystick 82 is provided on an end face 80c of the operation unit 80 that intersects with the outer peripheral surface 80a. The operator can operate the joystick 82 with their finger while grasping the outer peripheral surface 80a of the operation unit 80 and pressing the enable switches 81 to enable movement of the manipulator arm 60. For example, as shown in FIG. 6, the operator operates the joystick 82 provided on the end face 80c of the operation unit 80 with their index finger, for example, while pressing the pair of enable switches 81 provided on the outer peripheral surface 80a of the operation unit 80 with their thumb and middle finger, for example. Thus, substantially constant distances between the operator's thumb and middle finger that grasp the operation unit 80 and the operator's index finger that operates the joystick 82 can be easily maintained. Which fingers are used to operate the enable switches 81 and the joystick 82 is not limited to the above example.

Figure 11:
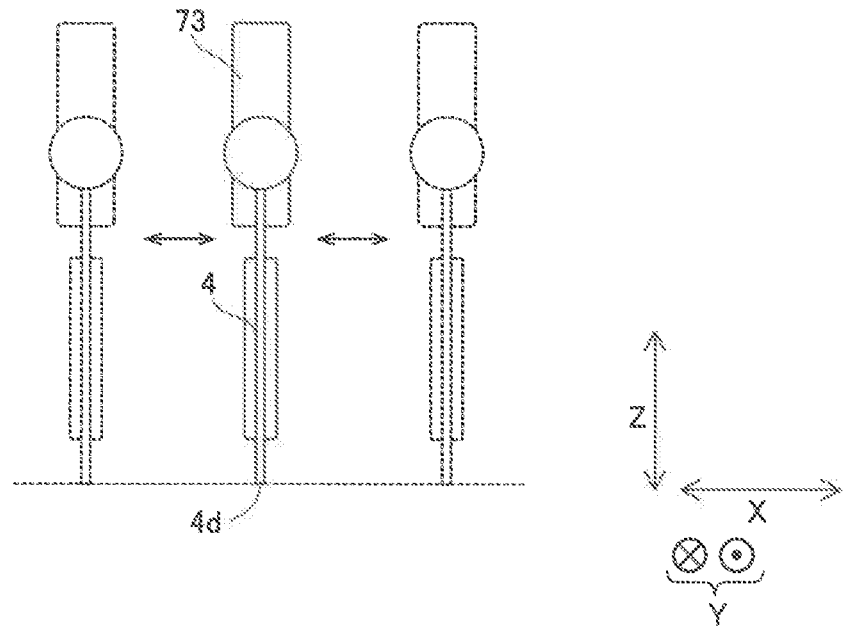
FIG. 11 is a diagram for illustrating translation of the manipulator arm.

With the joystick 82, movement of the surgical instrument 4 by the manipulator arm 60 is operated such that the tip end 4d of the surgical instrument 4 shown in FIG. 3 moves on a predetermined plane. The operation unit 80 includes the switch units 83 for the operator to operate movement of the surgical instrument 4 by the manipulator arm 60 such that the tip end 4d of the surgical instrument 4 moves along the longitudinal direction of the surgical instrument 4 orthogonal to the predetermined plane. The predetermined plane on which the tip end 4d of the surgical instrument 4 moves refers to an X-Y plane shown in FIG. 11 parallel to the end face 80c of the operation unit 80. The longitudinal direction of the surgical instrument 4 orthogonal to the predetermined plane refers to the Z direction orthogonal to the X-Y plane in FIG. 11. Coordinates represented by an X-axis, a Y-axis, and a Z-axis in FIG. 11 are referred to as a tool coordinate system or a base coordinate system. When the switch units 83 are pressed while the enable switches 81 are being pressed and movement of the surgical instrument 4 by the manipulator arm 60 is enabled, the tip end 4d of the surgical instrument 4 is moved along the longitudinal direction of the surgical instrument 4.

Each of the switch units 83 includes a switch 83a to move the tip end 4d of the surgical instrument 4 in the direction in which the surgical instrument 4 is inserted into the patient P along the longitudinal direction of the surgical instrument 4, and a switch 83b to move the tip end 4d of the surgical instrument 4 in a direction opposite to the direction in which the surgical instrument 4 is inserted into the patient P. Both the switch 83a and the switch 83b are push-button switches.

As shown in FIG. 5, the switch units 83 are provided on the opposite sides of the outer peripheral surface 80a of the operation unit 80. Specifically, the switch units 83 are provided on the surfaces 80b along the longitudinal direction of the substantially prismatic operation unit 80, respectively. That is, a pair of switches 83a and a pair of switches 83b are provided on opposite side surfaces of the operation unit 80.

Figure 12:
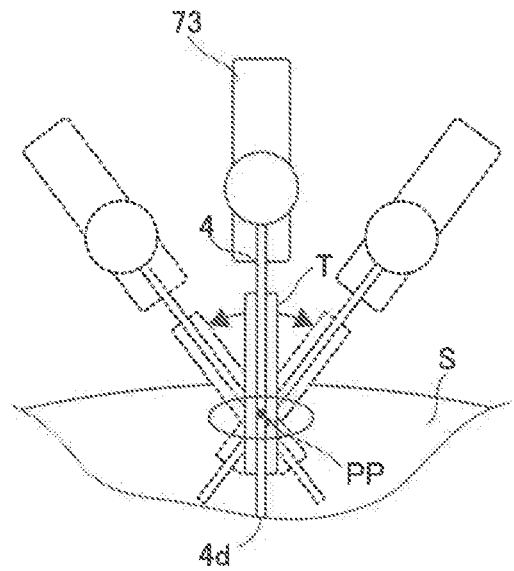
FIG. 12 is a diagram for illustrating rotation of the manipulator arm.

When the switch units 83 are operated, the arm portion 61 is moved such that the tip end 4d of the surgical instrument 4 is translated until the tip end 4d of the surgical instrument 4 is moved to the vicinity of a pivot position PP shown in FIG. 12, and after the tip end 4d of the surgical instrument 4 is moved to the vicinity of the pivot position PP, the translation mechanism 70 is moved such that the tip end 4d of the surgical instrument 4 is translated. Specifically, when the switch units 83 are operated, the arm portion 61 is moved such that the tip end 4d of the surgical instrument 4 is translated until the tip end 4d of the surgical instrument 4 is moved by a certain distance from the pivot position PP. After the tip end 4d of the surgical instrument 4 is moved by the certain distance from the pivot position PP, the translation mechanism 70 is moved such that the tip end 4d of the surgical instrument 4 is translated. That is, after the tip end 4d of the surgical instrument 4 is moved by the certain distance from the pivot position PP, the arm portion 61 is not moved but only the translation mechanism 70 is moved. The pivot position PP is described below.

In the first embodiment, as shown in FIG. 4, the operation unit 80 includes pivot buttons 85 to set the pivot position PP that serves as a fulcrum for movement of the surgical instrument 4 attached to the manipulator arm 60 shown in FIG. 12. The pivot buttons 85 are provided adjacent to the enable switches 81 on the surfaces 80b of the operation unit 80.

Figure 7:
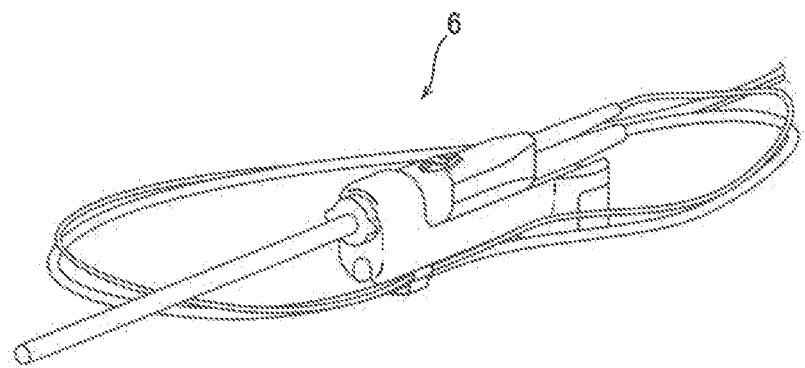
FIG. 7 is a diagram showing an endoscope.
Figure 8:
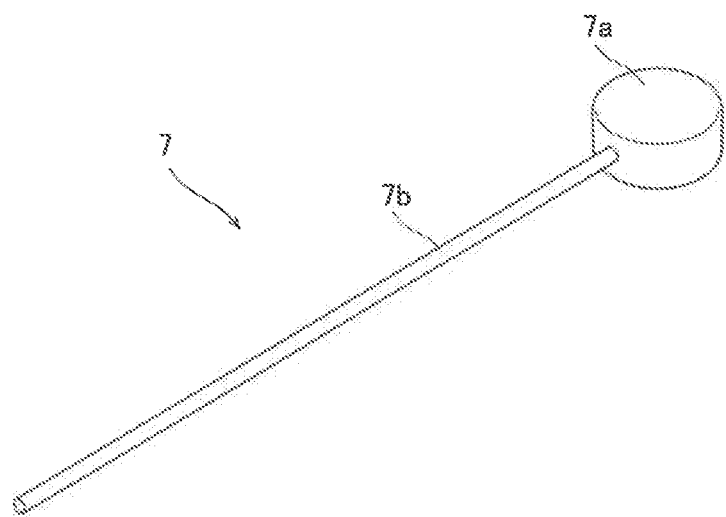
FIG. 8 is a diagram showing a pivot position setting instrument.

As shown in FIG. 7, the endoscope 6 attached to the tip end of the manipulator arm 60 when the pivot position PP is stored is actually used during surgery. On the other hand, as shown in FIG. 8, a pivot position setting instrument 7 attached to the tip end of the manipulator arm 60 when the pivot position PP is stored is a dummy that mimics the surgical instrument 4 such as a pair of forceps actually used during surgery. The pivot position setting instrument 7 includes a portion 7a that mimics the driven unit 4a and a portion 7b that mimics the shaft 4c. The tip end of the portion 7b of the pivot position setting instrument 7 does not have a pointed shape.

Figure 9:
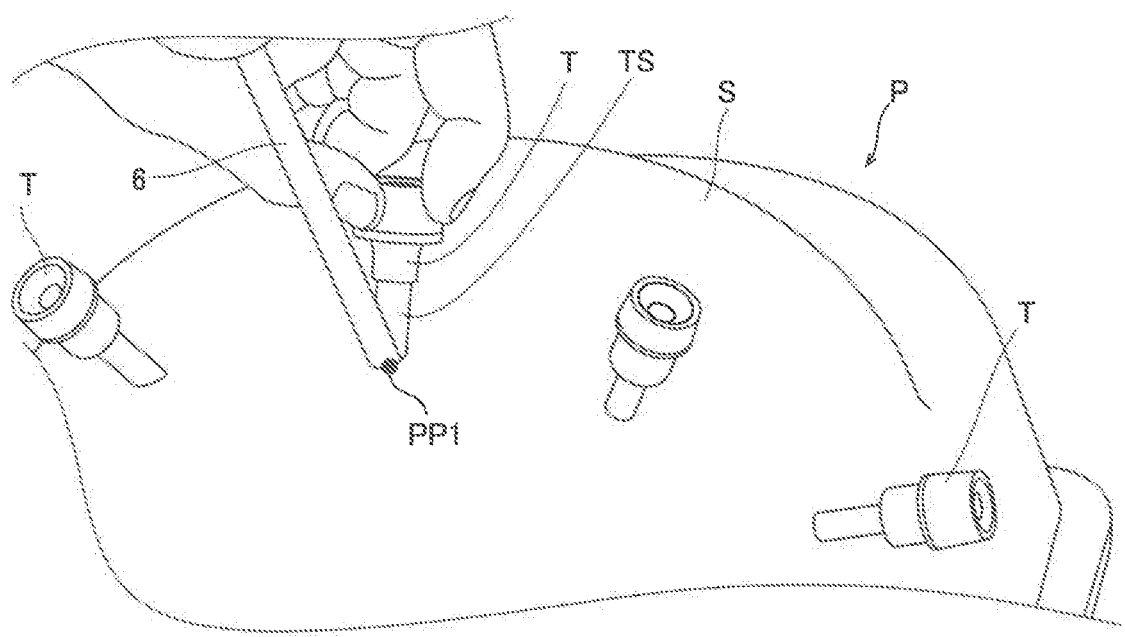
FIG. 9 is a diagram showing a state in which the tip end of the endoscope is moved to a position at which the outer surface of a trocar and the body surface of a patient contact each other.

In the first embodiment, when the tip end of the endoscope 6 or the pivot position setting instrument 7 attached to the tip end of the manipulator arm 60 is moved to a position at which the outer surface TS of the trocar T inserted into the body surface S of the patient P and the body surface S contact each other, as shown in FIG. 9, and the pivot buttons 85 are pressed, a temporary pivot position PP1 is stored in the storage 32. That is, when the endoscope 6 or the pivot position setting instrument 7 is not inserted into the trocar T but the tip end of the endoscope 6 or the pivot position setting instrument 7 is arranged on the side of the outer surface TS of the trocar T and in the vicinity of the body surface S, and the pivot buttons 85 are pressed, the temporary pivot position PP1 is stored in the storage 32. The vicinity of the body surface S indicates a concept including the body surface S itself and the surroundings of the body surface S. Setting of the pivot position PP based on the temporary pivot position PP1 is described below.

When the joystick 82 is operated, the tip end of the endoscope 6 or the pivot position setting instrument 7 attached to the tip end of the manipulator arm 60 is moved to a position corresponding to the insertion position of the trocar T inserted into the body surface S of the patient P. Specifically, the joystick 82 and the switch units 83 are operated while the enable switches 81 are being pressed such that the tip end of the endoscope 6 or the pivot position setting instrument 7 is moved.

As shown in FIG. 1, the endoscope 6 is attached to one (a manipulator arm 60c, for example) of the plurality of manipulator arms 60, and surgical instruments 4 other than the endoscope 6 are attached to the remaining manipulator arms 60 (manipulator arms 60a, 60b, and 60d, for example). Specifically, in surgery, the endoscope 6 is attached to one of four manipulator arms 60, and the surgical instruments 4 (such as pairs of forceps) other than the endoscope 6 are attached to the remaining three manipulator arms 60. The pivot position PP is stored in the storage 32 with the endoscope 6 attached to the manipulator arm 60 to which the endoscope 6 is to be attached. Furthermore, pivot positions PP are stored in the storage 32 with pivot position setting instruments 7 attached to the manipulator arms 60 to which the surgical instruments 4 other than the endoscope 6 are to be attached. The endoscope 6 is attached to one of the two manipulator arms 60b and 60c arranged in the center among the four manipulator arms 60 arranged adjacent to each other.

As shown in FIG. 5, the pivot buttons 85 are provided on the opposite sides of the outer peripheral surface 80a of the operation unit 80. Specifically, the cross-section of the operation unit 80 has a substantially rectangular shape, and the pivot buttons 85 are provided on the surfaces 80b of the operation unit 80 that face each other, respectively.

Figure 10:
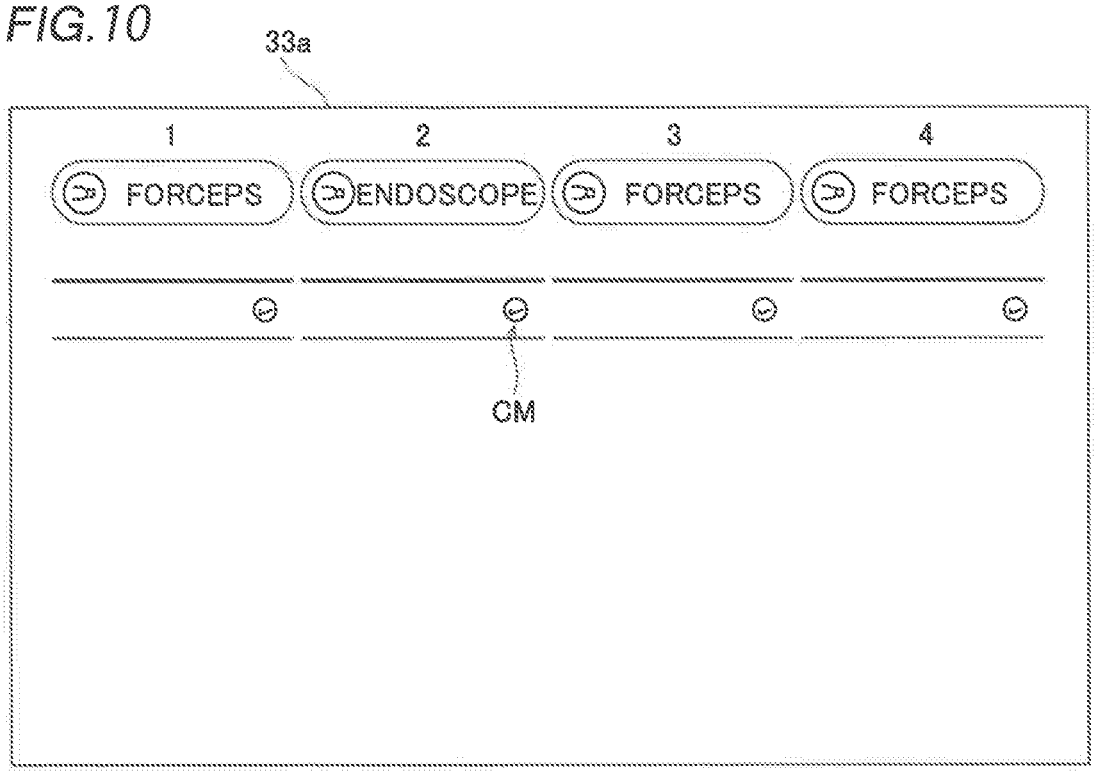
FIG. 10 is a diagram showing a display screen of a display.

As shown in FIG. 10, a display 33a is provided to display whether or not the pivot positions PP of the plurality of manipulator arms 60 have been stored. The display 33a is provided on the input 33 of the medical cart 3. The display 33a includes a liquid crystal panel, for example. Numbers 1, 2, 3, and 4 corresponding to the plurality of manipulator arms 60a, 60b, 60c, and 60d, respectively, are displayed on the display 33a. Furthermore, the types of surgical instruments 4 such as an endoscope 6 and a pair of forceps respectively attached to the plurality of manipulator arms 60 are displayed on the display 33*a*. When the pivot position PP is stored, a check mark CM is displayed for each of the plurality of manipulator arms 60.

As shown in FIG. 4, adjustment buttons 86 are provided on the surfaces 80*b* of the operation unit 80 to optimize the position of the manipulator arm 60. After the pivot position PP for the manipulator arm 60 to which the endoscope 6 has been attached is stored, the adjustment buttons 86 are pressed such that the positions of the other manipulator arms 60 and the arm base 50 are optimized.

As shown in FIG. 4, the operation unit 80 includes a mode switching button 84 to switch between a mode for translating the surgical instrument 4 attached to the arm manipulator 60 as shown in FIG. 11 and a mode for rotationally moving the surgical instrument 4 as shown in FIG. 12. In the operation unit 80, the mode switching button 84 is arranged in the vicinity of the joystick 82. Specifically, on the end face 80*c* of the operation unit 80, the mode switching button 84 is provided adjacent to the joystick 82. The mode switching button 84 is a push-button switch. Furthermore, a mode indicator 84*a* is provided in the vicinity of the mode switching button 84. The mode indicator 84*a* indicates a switched mode. Specifically, the mode indicator 84*a* is turned on to indicate a rotational movement mode and is turned off to indicate a translational mode.

The mode indicator 84*a* also serves as a pivot position indicator that indicates that the pivot position PP has been stored. Specifically, when the pivot position PP is stored, the mode indicator 84*a* continues to be on, and even when the mode switching button 84 is pressed, the mode indicator 84*a* is not turned off. Thus, the mode indicator 84*a* indicates that only the rotational movement mode is possible for the surgical instrument 4 attached to the manipulator arm 60, and the pivot position PP has been stored. The surgical instrument 4 attached to the manipulator arm 60 to be reset is removed, and the pivot buttons 85 are pressed and held such that the pivot position PP is reset.

As shown in FIG. 11, in the mode for translating the manipulator arm 60, the manipulator arm 60 is moved such that the tip end 4*d* of the surgical instrument 4 moves on the X-Y plane. As shown in FIG. 12, in the mode for rotationally moving the manipulator arm 60, when the pivot position PP is not stored, the manipulator arm 60 is moved such that the surgical instrument 4 rotationally moves about the end effector 4*b*, and when the pivot position PP is stored, the manipulator arm 60 is moved such that the surgical instrument 4 rotationally moves about the pivot position PP as a fulcrum. The surgical instrument 4 is rotationally moved while the shaft 4*c* of the surgical instrument 4 is inserted into the trocar T.

As shown in FIG. 3, the operation unit 80 is provided on the translation mechanism 70. The operation unit 80 is attached to the translation mechanism 70 so as to be adjacent to the surgical instrument 4 attached to the translation mechanism 70. Specifically, the operation unit 80 is attached to the tip end side link 73 of the translation mechanism 70. The operation unit 80 is arranged adjacent to the driven unit 4*a* of the surgical instrument 4.

As shown in FIG. 13, the manipulator arm 60 includes a plurality of servomotors M1, encoders E1, and speed reducers so as to correspond to a plurality of joints 64 of the arm portion 61. The encoders E1 detect the rotation angles of the servomotors M1. The speed reducers slow down rotation of the servomotors M1 to increase the torques.

As shown in FIG. 13, the translation mechanism 70 includes a plurality of servomotor M2 to rotate the rotary bodies provided in the driven unit 4*a* of the surgical instrument 4, the servomotor M3 to translate the surgical instrument 4, a plurality of encoders E2, an encoder E3, and a plurality of speed reducers. The encoders E2 and E3 detect the rotation angles of the servomotors M2 and M3, respectively. The speed reducers slow down rotation of the servomotors M2 and M3 to increase the torques.

The positioner 40 includes a plurality of servomotors M4, encoders E4, and speed reducers so as to correspond to a plurality of joints 43 of the positioner 40. The encoders E4 detect the rotation angles of the servomotors M4. The speed reducers slow down rotation of the servomotors M4 to increase the torques.

The medical cart 3 includes servomotors M5 to drive a plurality of front wheels of the medical cart 3, respectively, encoders E5, and speed reducers. The encoders E5 detect the rotation angles of the servomotors M5. The speed reducers slow down rotation of the servomotors M5 to increase the torques.

The controller 31 of the medical cart 3 includes an arm controller 31*a* to control movement of the plurality of manipulator arms 60 based on commands, and a positioner controller 31*b* to control movement of the positioner 40 and driving of the front wheels of the medical cart 3 based on commands. Servo controllers C1 that control the servomotors M1 to drive the manipulator arm 60 are electrically connected to the arm controller 31*a*. The encoders E1 that detect the rotation angles of the servomotors M1 are electrically connected to the servo controllers C1.

Servo controllers C2 that control the servomotors M2 to drive the surgical instrument 4 are electrically connected to the arm controller 31*a*. The encoders E2 that detect the rotation angles of the servomotors M2 are electrically connected to the servo controllers C2. A servo controller C3 that controls the servomotor M3 to translate the translation mechanism 70 is electrically connected to the arm controller 31*a*. The encoder E3 that detects the rotation angle of the servomotor M3 is electrically connected to the servo controller C3.

An operation command input to the remote control apparatus 2 is input to the arm controller 31*a*. The arm controller 31*a* generates a position command based on the input operation command and the rotation angle detected by the encoder E1, E2, or E3, and outputs the position command to the servo controller C1, C2, or C3. The servo controller C1, C2, or C3 generates a current command based on the position command input from the arm controller 31*a* and the rotation angle detected by the encoder E1, E2, or E3, and outputs the current command to the servomotor M1, M2, or M3. Thus, the manipulator arm 60 is moved according to the operation command input to the remote control apparatus 2.

The arm controller 31*a* of the controller 31 operates the manipulator arm 60 based on an input signal from the joystick 82 of the operation unit 80. Specifically, the arm controller 31*a* generates position commands based on the input signal (operation command) input from the joystick 82 and the rotation angles detected by the encoders E1, and outputs the position commands to the servo controllers C1. The servo controllers C1 generate current commands based on the position commands input from the arm controller 31*a* and the rotation angles detected by the encoders E1, and output the current commands to the servomotors M1. Thus, the manipulator arm 60 is moved according to the operation command input to the joystick 82.

The arm controller 31*a* operates the manipulator arm 60 based on an input signal from each of the switch units 83 of the operation unit 80. Specifically, the arm controller 31*a* generates a position command based on the input signal (operation command) input from each of the switch units 83 and the rotation angle detected by the encoder E1 or E3, and outputs the position command to the servo controller C1 or C3. The servo controller C1 or C3 generates a current command based on the position command input from the arm controller 31*a* and the rotation angle detected by the encoder E1 or E3, and outputs the current command to the servomotor M1 or M3. Thus, the manipulator arm 60 is moved according to the operation command input to each of the switch units 83.

The arm controller 31*a* of the controller 31 performs a control to reduce a change in the moving speed of the manipulator arm 60 by performing at least one of setting an upper limit for the input signal from the joystick 82 or smoothing the input signal from the joystick 82. Specifically, the controller 31 controls movement of the manipulator arm 60 using the upper limit as the input signal when the upper limit is set for the input signal from the joystick 82, and an input signal exceeding the upper limit is input. Furthermore, the controller 31 smooths the input signal from the joystick 82 by a low-pass filter (LPF), for example. In the first embodiment, the controller 31 performs both of setting the upper limit for the input signal from the joystick 82 and smoothing the input signal from the joystick 82.

As shown in FIG. 13, servo controllers C4 that control the servomotors M4 to move the positioner 40 are electrically connected to the positioner controller 31*b*. The encoders E4 that detect the rotation angles of the servomotors M4 are electrically connected to the servo controllers C4. Servo controllers C5 that control the servomotors M5 to drive the front wheels of the medical cart 3 are electrically connected to the positioner controller 31*b*. The encoders E5 that detect the rotation angles of the servomotors M5 are electrically connected to the servo controllers C5.

An operation command related to setting a preparation position, for example, is input from the input 33 to the positioner controller 31*b*. The positioner controller 31*b* generates position commands based on the operation command input from the input 33 and the rotation angles detected by the encoders E4, and outputs the position commands to the servo controllers C4. The servo controllers C4 generate current commands based on the position commands input from the positioner controller 31*b* and the rotation angles detected by the encoders E4, and output the current commands to the servomotors M4. Thus, the positioner 40 is moved according to the operation command input to the input 33. Similarly, the positioner controller 31*b* moves the medical cart 3 based on the operation command from the input 33.

Setting of the pivot position PP is now described.

Figure 14:
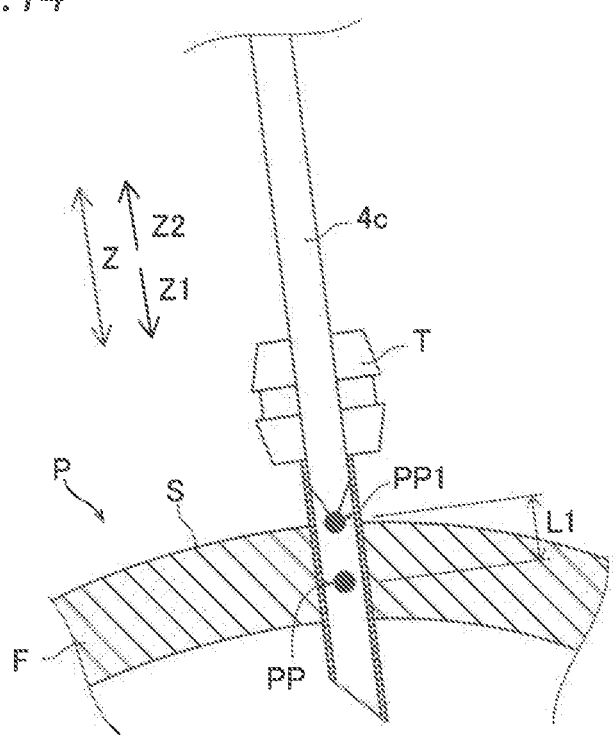
FIG. 14 is a diagram for illustrating adjustment of a pivot position according to the first embodiment.

In the first embodiment, as shown in FIG. 14, the controller 31 sets the temporary pivot position PP1 based on an operation on the pivot buttons 85, stores it in the storage 32, and stores a position adjusted by a predetermined length L1 from the temporary pivot position PP1 as the pivot position PP in the storage 32. The pivot buttons 85 are examples of a pivot position setter.

Specifically, as shown in FIG. 9, the tip end of the endoscope 6 shown in FIG. 7 corresponding to the surgical instrument 4 attached to the tip end of the manipulator arm 60 or the pivot position setting instrument 7 shown in FIG. 8 is moved to a position corresponding to the insertion position of the trocar T inserted into the body surface S of the patient P with the operation unit 80. Then, the pivot buttons 85 are pressed. Thus, the temporary pivot position PP1 is set. Then, the position adjusted by the predetermined length L1 from the temporary pivot position PP1 is stored as the pivot position PP in the storage 32. The pivot position PP is set as one point, and in the setting of the pivot position PP, the direction of the surgical instrument 4 is not set.

In the first embodiment, as shown in FIG. 14, the controller 31 stores the position adjusted by the predetermined length L1 along a direction in which the surgical instrument 4 extends from the temporary pivot position PP1 as the pivot position PP in the storage 32. The direction in which the surgical instrument 4 extends refers to the Z direction. The pivot position PP is a point that is moved by the predetermined length L1 to the Z1 side, which is the tip end side of the surgical instrument 4, or the Z2 side, which is the base end side of the surgical instrument 4, from the temporary pivot position PP1.

Figure 15:
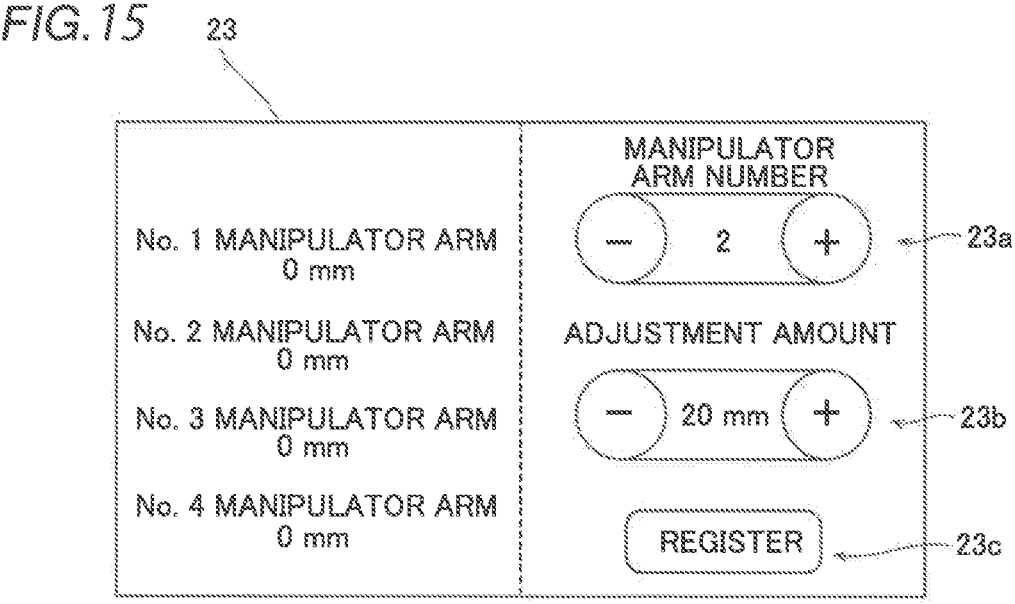
FIG. 15 is a diagram showing a touch panel for inputting the adjustment amount of the pivot position.

In the first embodiment, as shown in FIG. 15, the medical manipulator 1 includes the touch panel 23 for the operator to input the predetermined length L1 in advance. The controller 31 stores the position adjusted by the predetermined length L1 input in advance from the temporary pivot position PP1 as the pivot position PP in the storage 32. The term "in advance" refers to before the pivot position PP is set.

Specifically, in the first embodiment, the touch panel 23 is arranged on the remote control apparatus 2. The touch panel 23 includes a selector 23*a* for the operator to select the number of the manipulator arm 60. One of 1, 2, 3, and 4 is selected as the number of the manipulator arm 60. The manipulator arm numbers 1 to 4 correspond to the manipulator arms 60*a* to 60*d*, respectively. The touch panel 23 includes an adjustment amount input 23*b* for the operator to input an adjustment amount. The adjustment amount refers to the predetermined length L1. It is possible to input a length up to a predetermined limit into the adjustment amount input 23*b*. The predetermined limit is −10 mm or more and +30 mm or less, for example. The touch panel 23 includes a registration button 23*c*. The operator selects the number of the manipulator arm 60, inputs the adjustment amount, and then presses the registration button 23*c*.

Figure 16:
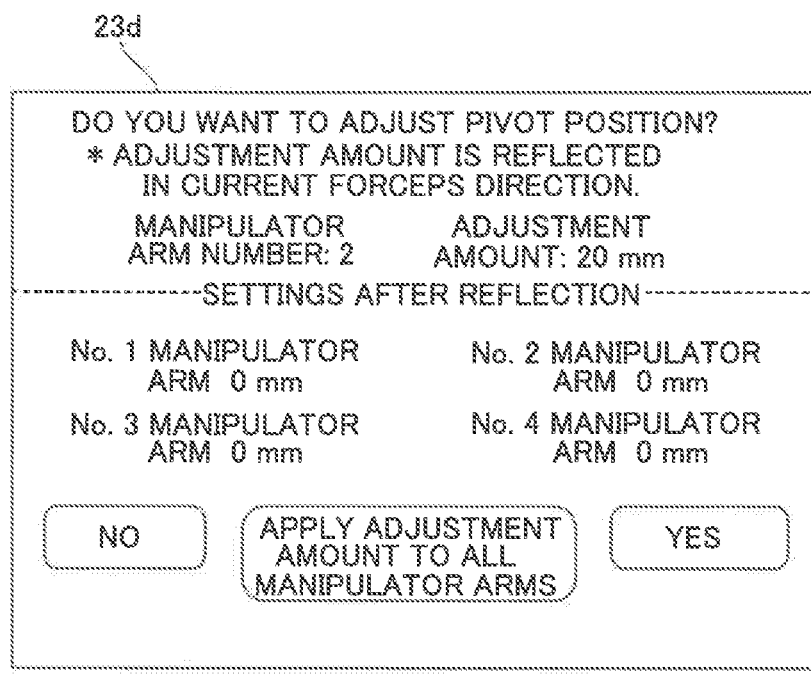
FIG. 16 is a diagram showing an inquiry screen for the adjustment amount of the pivot position.

As shown in FIG. 16, when the registration button 23*c* is pressed, an inquiry screen 23*d* is displayed on the touch panel 23 of the remote control apparatus 2. The inquiry screen 23*d* is used to query the operator regarding whether or not to allow a change in the pivot position PP. On the inquiry screen 23*d*, the number of the manipulator arm 60 to be changed in the pivot position PP and the adjustment amount are displayed. Furthermore, the adjustment amount is displayed for each manipulator arm 60. On the inquiry screen 23*d*, buttons for "YES", "NO", and "APPLY ADJUSTMENT AMOUNT TO ALL MANIPULATOR ARMS" are displayed. When the YES button is pressed, the adjustment amount is stored in the storage 32. When the NO button is pressed, the adjustment amount is not stored in the storage 32. When the APPLY ADJUSTMENT AMOUNT TO ALL MANIPULATOR ARMS button is pressed, the adjustment amount specified when the registration button 23*c* is pressed is stored as the adjustment amounts of all the manipulator arms 60 in the storage 32.

Thus, in the first embodiment, the controller 31 stores the position adjusted by the predetermined length L1 from the temporary pivot position PP1 as the pivot position PP in the storage 32 for each of the manipulator arms 60*a* to 60*d*.

As shown in FIG. 14, it is preferable to set the pivot position PP at a central portion of the abdominal wall F of the patient P in the thickness direction. Therefore, the operator inputs the adjustment amount such that the pivot position PP is set at the central portion of the abdominal wall F of the patient P in the thickness direction. For example, for the patient P having a small thickness of the abdominal wall F, the operator sets a relatively small adjustment amount. For the patient P having a large thickness of the abdominal wall F, the operator sets a relatively large adjustment amount. Thus, the controller 31 adjusts the temporary pivot position PP1 such that the pivot position PP is located at the central portion of the abdominal wall F of the patient P in the thickness direction. Then, the controller 31 stores the adjusted pivot position PP in the storage 32. The central portion indicates a concept including the center and the vicinity of the center.

In the first embodiment, as shown in FIG. 14, the touch panel 23 receives a change in the pivot position PP. After the pivot position PP is stored in the storage 32, the controller 31 stores the changed and received pivot position PP in the storage 32 when the touch panel 23 receives the change in the pivot position PP. Specifically, the touch panel 23 receives the amount of change from the current pivot position PP. Then, the controller 31 stores a position moved by the amount of change along the Z direction in which the surgical instrument 4 extends as the changed pivot position PP in the storage 32.

More specifically, after the pivot position PP is set once, the pivot position PP is changed during surgery, for example. On the touch panel 23, the selector 23a, the adjustment amount input 23b, and the registration button 23c are displayed as before the pivot position PP is set. The operator selects the number of the manipulator arm 60 to be changed in the pivot position PP through the selector 23a. Furthermore, the operator inputs the amount of change in the pivot position PP through the adjustment amount input 23b. Then, the operator presses the registration button 23c. When the registration button 23c is pressed, the inquiry screen 23d shown in FIG. 16 is displayed on the touch panel 23 of the remote control apparatus 2.

Figure 17:
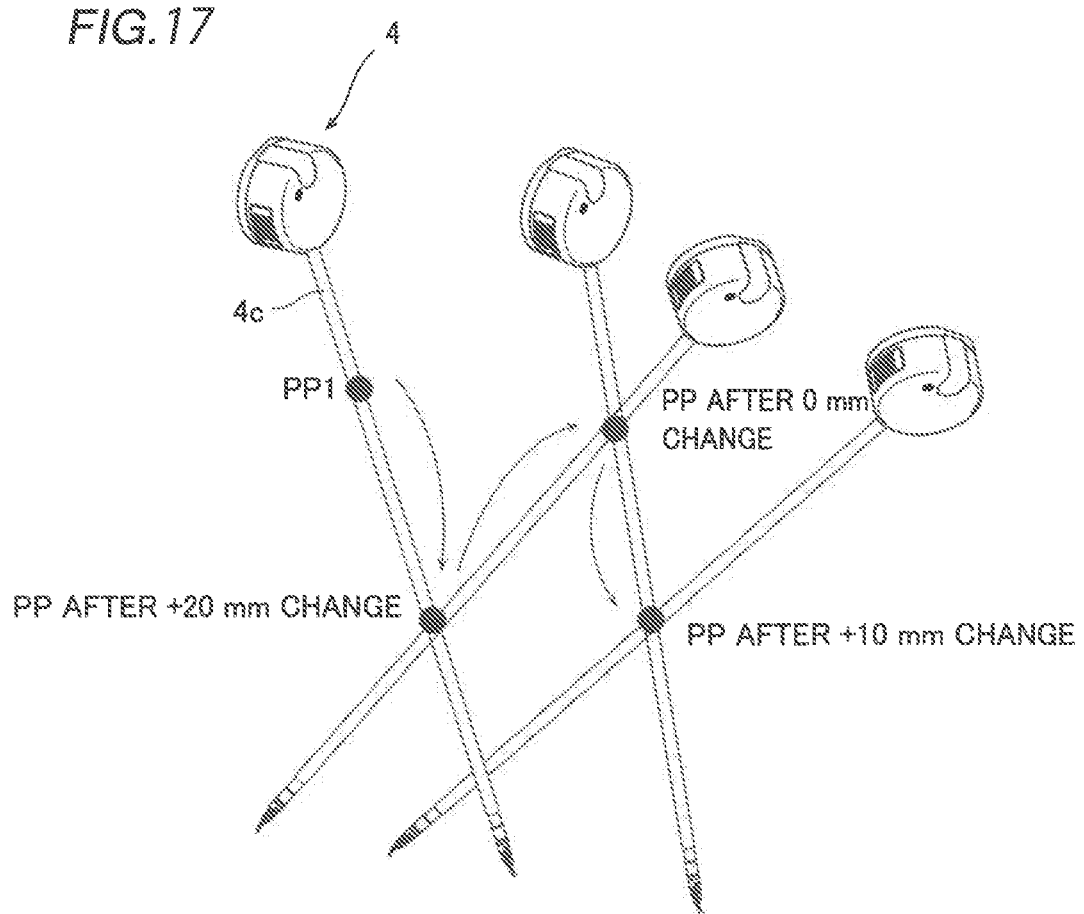
FIG. 17 is a diagram for illustrating a change in the pivot position.

For example, as shown in FIG. 17, when the pivot position PP is changed in the X and Y directions (see FIG. 11), the joystick 82 is operated by the operator (such as a nurse or an assistant) in a direction in which the pivot position PP is desired to be moved. At this time, a point moved to the tip end side of the surgical instrument 4 by +20 mm from the temporary pivot position PP1 is set as the pivot position PP. Then, the touch panel 23 receives a change to set the pivot position PP to 0 mm. Thus, the pivot position PP is changed to a point that is moved to the base end side of the surgical instrument 4 by −20 mm. Furthermore, the pivot position PP is moved along a direction in which the shaft 4c extends in the current posture of the surgical instrument 4. Then, the operator changes the posture of the surgical instrument 4 such that the longitudinal direction of the surgical instrument 4 is parallel to the desired pivot position PP. Furthermore, the touch panel 23 receives a change to set the pivot position PP to +10 mm. Thus, the pivot position PP is changed to a point that is moved in the X and Y directions and moved to the tip end side of the surgical instrument 4 by +10 mm.

The change in the pivot position PP is not received when the operator is looking into the monitor 24, but is received when the operator's head is moved away from the monitor 24. Whether or not the operator is looking into the monitor 24 is detected by a sensor 241 shown in FIG. 1. Furthermore, the monitor 24 may display that the pivot position PP has been changed.

When the operator looks into the monitor 24 after pressing the YES button on the inquiry screen 23d, the pivot position PP may be changed as long as the controller 31 has completed the change in the pivot position PP. When the operator looks into the monitor 24 after pressing the YES button on the inquiry screen 23d, the pivot position PP may not be changed unless the controller 31 has completed the change in the pivot position PP.

When the operator operates the operation arms 21 after pressing the YES button on the inquiry screen 23d, the pivot position PP may be changed as long as the controller 31 has completed the change in the pivot position PP. When the operator operates the operation arms 21 after pressing the YES button on the inquiry screen 23d, the pivot position PP may not be changed unless the controller 31 has completed the change in the pivot position PP.

A method for the medical manipulator 1 to set the pivot position is now described. The endoscope 6 is attached to one of the four manipulator arms 60, and the pivot position setting instruments 7 are attached to the remaining manipulator arms 60. The trocar T is inserted in the body surface S of the patient P.

Figure 18:
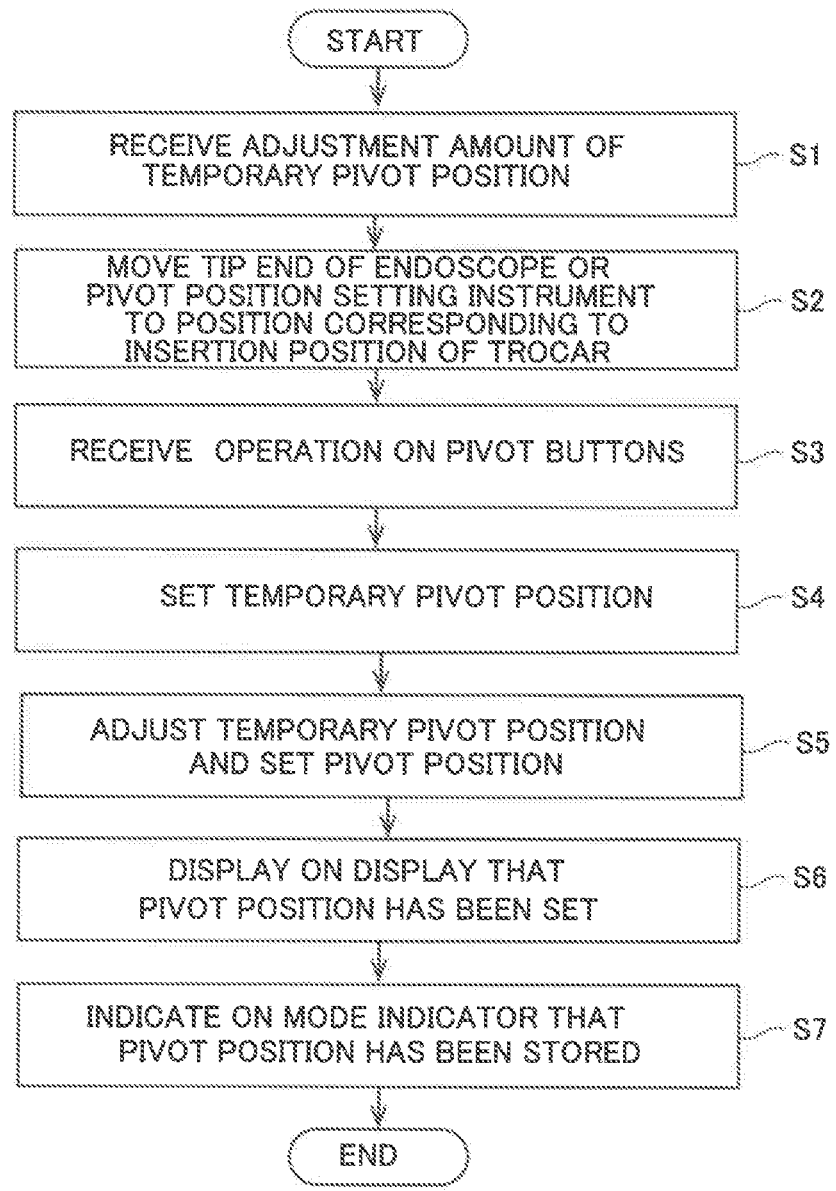
FIG. 18 is a flowchart for illustrating a method for setting the pivot position according to the first embodiment.

First, as shown in FIG. 18, in step S1, the touch panel 23 receives an input of the adjustment amount for each manipulator arm 60.

Then, in step S2, with the operation unit 80, the tip end of the endoscope 6 attached to the tip end of the manipulator arm 60 is moved to the position corresponding to the insertion position of the trocar T inserted into the body surface S of the patient P, as shown in FIG. 9. Specifically, the tip end of the endoscope 6 is moved to a position at which the outer surface TS of the trocar T inserted into the body surface S of the patient P and the body surface S contact each other.

Then, in step S3, the pivot buttons 85 are pressed with the tip end of the endoscope 6 moved to the position corresponding to the insertion position of the trocar T. Thus, the controller 31 receives the operation on the pivot buttons 85.

Then, in step S4, in the first embodiment, as shown in FIG. 14, the controller 31 sets the temporary pivot position PP1 based on the operation on the pivot buttons 85 and stores it in the storage 32.

Then, in step S5, in the first embodiment, the controller 31 stores the position adjusted by the predetermined length L1 from the set temporary pivot position PP1 as the pivot position PP in the storage 32.

Then, in step S6, the display 33a displays that the pivot position PP of the manipulator arm 60 has been stored. Specifically, the check mark CM is displayed below the number corresponding to the manipulator arm 60 to which the endoscope 6 is attached.

Then, in step S7, the mode indicator 84a of the operation unit 80 indicates that the pivot position PP has been stored. Specifically, the mode indicator 84a of the operation unit 80 attached to the manipulator arm 60 to which the endoscope 6 is attached is turned on.

Thus, the pivot position PP is first set for one manipulator arm 60 to which the endoscope 6 is attached. Then, step S2 to step S7 described above are repeated such that the pivot positions PP are set for the remaining manipulator arms 60 to which the pivot position setting instruments 7 are attached.

The procedure of surgery using the medical manipulator 1 is now described. In the surgery using the medical manipulator 1, the medical cart 3 is first moved to a predetermined position in the operating room by the operator (such as a nurse or an assistant). Next, the operator operates a touch panel of the input 33 to operate the positioner 40 such that the arm base 50 and a surgical table 5 or the patient P have a desired positional relationship so as to move the arm base 50. Furthermore, the manipulator arm 60 is moved such that the trocar T arranged on the body surface of the patient P and the surgical instrument 4 have a predetermined positional relationship. The trocar T is a working channel for inserting a surgical instrument or the like into the body cavity. The joysticks 82 and the switch units 83 are operated by the operator such that the plurality of manipulator arms 60 are moved to desired positions. Then, the pivot positions PP are set as described above. Then, with the positioner 40 being stationary, the plurality of manipulator arms 60 and the surgical instruments 4 are operated based on commands from the remote control apparatus 2. Thus, the surgery with the medical manipulator 1 is performed.

Advantages of First Embodiment

According to the first embodiment, the following advantages are achieved.

According to the first embodiment, as described above, the controller 31 is configured or programmed to set the temporary pivot position PP1 based on the operation on the pivot buttons 85 and store the position adjusted by the predetermined length L1 from the temporary pivot position PP1 as the pivot position PP in the storage 32. Accordingly, the position adjusted by the predetermined length L1 from the temporary pivot position PP1 set on the body surface S of the patient P can be used as the pivot position PP. For example, the pivot position PP can be set closer to the center of the abdominal wall F than the body surface S of the patient P. Therefore, the pivot position PP can be set to an appropriate position.

According to the first embodiment, as described above, the controller 31 is configured or programmed to store the position adjusted by the predetermined length L1 along the direction in which the surgical instrument 4 extends from the temporary pivot position PP1 as the pivot position PP in the storage 32. Accordingly, the temporary pivot position PP1 is adjusted by the predetermined length L1 along the direction in which the surgical instrument 4 extends such that the pivot position PP can be easily set closer to the center of the abdominal wall F than the body surface S of the patient P.

According to the first embodiment, as described above, the controller 31 is configured or programmed to store the position adjusted by the predetermined length L1 input in advance from the temporary pivot position PP1 as the pivot position PP in the storage 32. Accordingly, the operator only needs to operate the pivot buttons 85 once in order to set the temporary pivot position PP1 and store the pivot position PP. Therefore, it is possible to significantly reduce or prevent a complex operation to set the pivot position PP, and thus it is possible to reduce the burden on the operator.

According to the first embodiment, as described above, the touch panel 23 is arranged on the remote control apparatus 2. Accordingly, the touch panel 23 is arranged in the vicinity of a doctor or the like who operates the remote control apparatus 2. Therefore, a doctor or the like can easily input the predetermined length L1 in advance.

According to the first embodiment, as described above, the controller 31 is configured or programmed to store the position adjusted by the predetermined length L1 from the temporary pivot position PP1 as the pivot position PP for each of the plurality of manipulator arms 60 in the storage 32. Accordingly, the pivot position PP can be appropriately set for each of the plurality of manipulator arms 60.

According to the first embodiment, as described above, the controller 31 is configured or programmed to store the changed and received pivot position PP in the storage 32 when the touch panel 23 receives a change in the pivot position PP after the pivot position PP is stored in the storage 32. Accordingly, even after the pivot position PP is once set, the operator such as a doctor can change the pivot position PP. Therefore, even when the patient P moves after the pivot position PP is once set, an appropriate pivot position PP can be set.

According to the first embodiment, as described above, the touch panel 23 receives the amount of change from the pivot position PP, and the controller 31 is configured or programmed to store the position moved by the amount of change along the direction in which the surgical instrument 4 extends as the changed pivot position PP in the storage 32. Accordingly, the pivot position PP can be changed simply by moving the pivot position PP by the received amount of change. Therefore, the control load of the controller 31 can be reduced.

According to the first embodiment, as described above, the controller 31 is configured or programmed to set the central portion of the abdominal wall F of the patient P in the thickness direction as the pivot position PP. Accordingly, the influence of rotation of the surgical instrument 4 about the pivot position PP as a fulcrum on the abdominal wall F of the patient P can be effectively reduced.

Second Embodiment

A method for setting a pivot position according to a second embodiment is now described.

Figure 19:
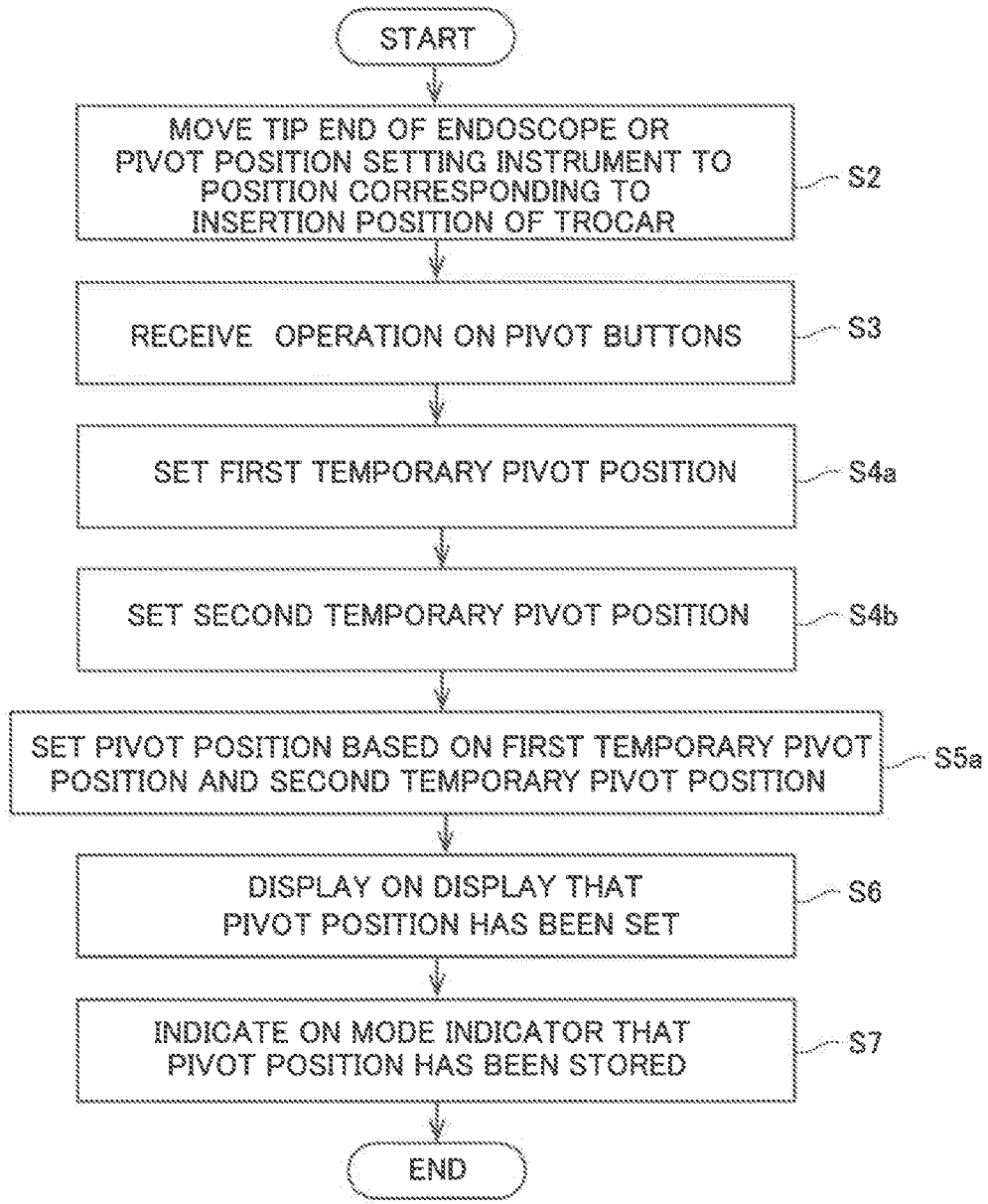
FIG. 19 is a flowchart for illustrating a method for setting a pivot position according to a second embodiment.

In the second embodiment, as shown in FIG. 19, step S1 of the first embodiment is not performed. Furthermore, the operations in step S2 and step S3 are the same as those in the first embodiment.

Figure 20:
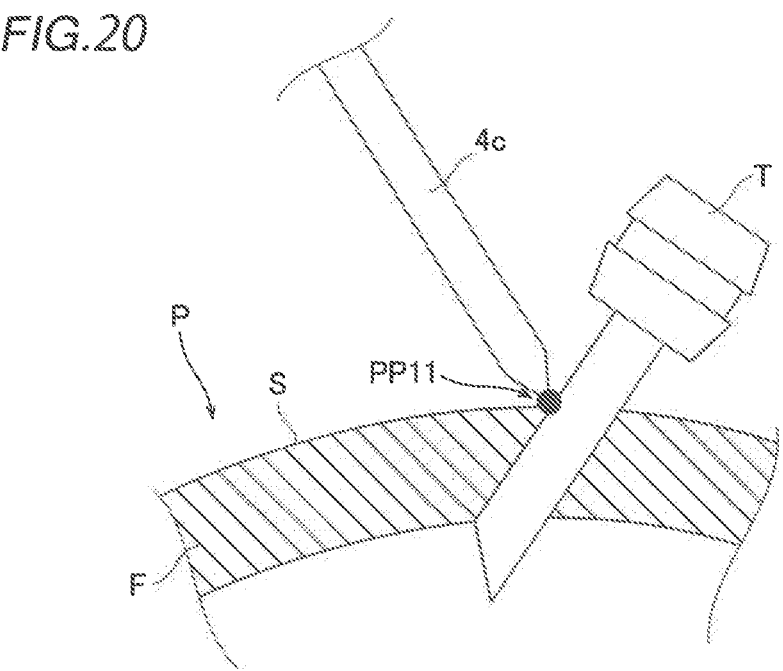
FIG. 20 is a diagram for illustrating setting of a first temporary pivot position according to the second embodiment.

In the second embodiment, in step S4a, as shown in FIG. 20, a controller 31 sets a first temporary pivot position PP11 when the tip end of a surgical instrument 4 attached to the tip end of a manipulator arm 60 is located at a position corresponding to the insertion position of a trocar T inserted into the body surface S of a patient P and pivot buttons 85 are operated.

Figure 21:
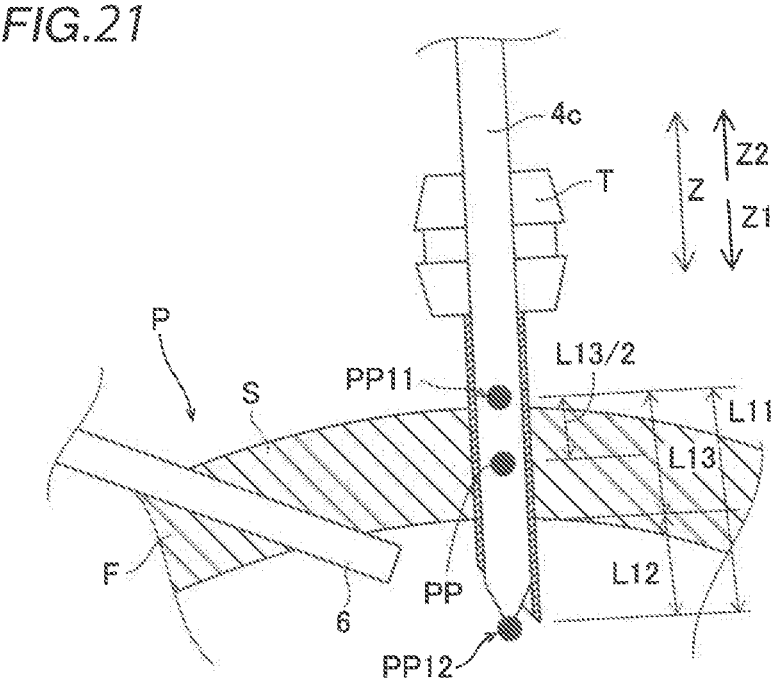
FIG. 21 is a diagram for illustrating adjustment of the pivot position according to the second embodiment.

Then, in step S4b, as shown in FIG. 21, when the tip end of the surgical instrument 4 is located at a position corresponding to the tip end of the trocar T located inside the body of the patient P and the pivot buttons 85 are operated, the controller 31 sets a second temporary pivot position PP12. An endoscope 6 is inserted in advance from the body surface S of the patient P. From an image captured by the endoscope 6, an operator confirms that the tip end of the surgical instrument 4 is located at the position corresponding to the tip end of the trocar T.

Figure 22:
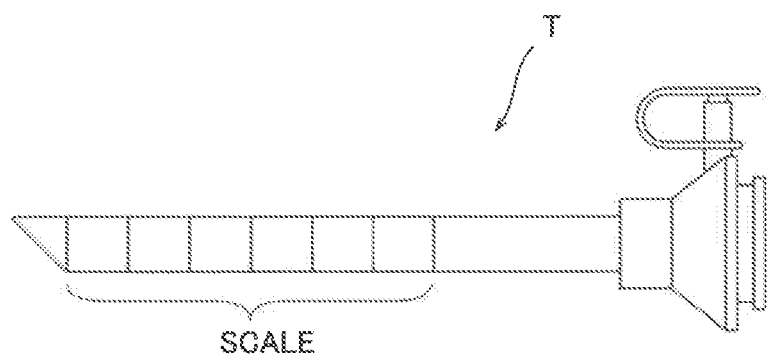
FIG. 22 is a diagram showing a trocar with a scale.

Then, in step S5a, the controller 31 stores a position adjusted based on the first temporary pivot position PP11 and the second temporary pivot position PP12 as a pivot position PP in a storage 32. Specifically, the controller 31 calculates a difference value L13 by subtracting the amount of protrusion L12 of the tip end of the trocar T from the abdominal wall F of the patient P to the inside of the body from a distance L11 between the first temporary pivot position PP11 and the second temporary pivot position PP12. Then, the controller 31 stores a position moved by ½ of the difference value L13 from the first temporary pivot position PP11 to the inside of the body of the patient P as the pivot position PP in the storage 32. The amount of protrusion L12 of the trocar T is a predetermined specified value. As shown in FIG. 22, the trocar T has a scale. The operator adjusts the amount of insertion of the trocar T while referring to the scale of the trocar T such that the amount of protrusion L12 becomes the specified value from an image captured by the endoscope 6. The difference value L13 is an example of a predetermined length.

The operations in step S6 and step S7 are the same as those in the first embodiment.

Advantages of Second Embodiment

According to the second embodiment, the following advantages are achieved.

According to the second embodiment, as described above, the controller 31 is configured or programmed to store the position adjusted based on the first temporary pivot position PP11 and the second temporary pivot position PP12 as the pivot position PP in the storage 32. Accordingly, even when the thickness of the abdominal wall F of the patient P is unknown, the pivot position PP can be appropriately set according to the thickness of the abdominal wall F of the patient P based on the first temporary pivot position PP11 and the second temporary pivot position PP12.

According to the second embodiment, as described above, the controller 31 is configured or programmed to store the position moved by ½ of the difference value L13 from the first temporary pivot position PP11 to the inside of the body of the patient P as the pivot position PP in the storage 32. The position moved by ½ of the difference value L13 from the first temporary pivot position PP11 to the inside of the body of the patient P corresponds to the center of the abdominal wall F of the patient P in the thickness direction. Therefore, the pivot position PP can be set at the center of the abdominal wall F of the patient P in the thickness direction.

Modified Examples

The embodiments disclosed this time must be considered as illustrative in all points and not restrictive. The scope of the present disclosure is not shown by the above description of the embodiments but by the scope of claims for patent, and all modifications (modified examples) within the meaning and scope equivalent to the scope of claims for patent are further included.

For example, while the position adjusted by the predetermined length L1 along the direction in which the surgical instrument 4 extends from the temporary pivot position PP1 is set as the pivot position PP in each of the aforementioned first and second embodiments, the present disclosure is not limited to this. For example, the direction in which adjustment is performed by the predetermined length L1 may alternatively be set in a vertical direction.

While the pivot position PP is set by the controller 31 of the medical cart 3 in each of the aforementioned first and second embodiments, the present disclosure is not limited to this. For example, the pivot position PP may alternatively be set by a control device other than the controller 31 of the medical cart 3.

While the touch panel 23 is arranged on the remote control apparatus 2 in the aforementioned first embodiment, the present disclosure is not limited to this. For example, the touch panel 23 may alternatively be arranged on a portion other than the remote control apparatus 2.

While the pivot position PP is stored by pressing the pivot buttons 85 in the aforementioned first embodiment, the present disclosure is not limited to this. For example, the pivot position PP may alternatively be stored by an operation other than pressing.

While the operator inputs the predetermined length L1 to the touch panel 23 in advance in the aforementioned first embodiment, the present disclosure is not limited to this. For example, the controller 31 may alternatively calculate the thickness of the abdominal wall F of the patient P based on a three-dimensional model created from an image of the patient P captured in advance, and store a position adjusted by a length corresponding to ½ of the thickness from the temporary pivot position PP1 as the pivot position PP in the storage 32. Specifically, the controller 31 acquires the three-dimensional model created from the image of the patient P captured by a CT scanner or the like. Then, the controller 31 calculates the thickness of the abdominal wall F of the patient P based on the three-dimensional model. Thus, the pivot position PP is set based on the three-dimensional model such that even when there are individual differences in the thickness of the abdominal wall F of the patient P, the pivot position PP can be appropriately set according to the thickness of the abdominal wall F of each patient P.

While the position moved from the first temporary pivot position PP11 by ½ of the difference value L13 obtained by subtracting the amount of protrusion L12 of the tip end of the trocar T from the distance L11 between the first temporary pivot position PP11 and the second temporary pivot position PP12 is set as the pivot position PP in the aforementioned second embodiment, the present disclosure is not limited to this. For example, a position moved from the first temporary pivot position PP11 by a length different from ½ of the difference value L13 may alternatively be set as the pivot position PP.

While the touch panel 23 receives both the predetermined length L1 and the amount of change in the pivot position PP in the aforementioned first embodiment, the present disclosure is not limited to this. For example, a receiver may alternatively be provided separately from the touch panel 23 for the operator to input the predetermined length L1 in advance in order to receive a change in the pivot position PP.

While the pivot position PP is set at the center of the abdominal wall F of the patient P in the thickness direction in each of the aforementioned first and second embodiments, the present disclosure is not limited to this. For example, the pivot position PP may alternatively be set on the side closer to the body surface S than the central portion of the abdominal wall F of the patient P in the thickness direction, or on the side farther from the body surface S than the central portion of the abdominal wall F of the patient P in the thickness direction.

While the pivot position PP is set in a state in which the pivot position setting instrument 7 is attached to the manipulator arm 60 in each of the aforementioned first and second embodiments, the present disclosure is not limited to this. In the present disclosure, the pivot position PP may alternatively be set in a state in which a pair of forceps or the like actually used is attached to the manipulator arm 60.

While four manipulator arms 60 are provided in each of the aforementioned first and second embodiments, the present disclosure is not limited to this. In the present disclosure, the number of manipulator arms 60 may alternatively be any number as long as at least one manipulator arm 60 is provided.

While each of the arm portion 61 and the positioner 40 includes a 7-axis articulated robot in each of the aforementioned first and second embodiments, the present disclosure is not limited to this. For example, each of the arm portion 61 and the positioner 40 may alternatively include an articulated robot having an axis configuration other than the 7-axis articulated robot. The axis configuration other than the 7-axis articulated robot refers to six axes or eight axes, for example.

While the medical manipulator 1 includes the medical cart 3, the positioner 40, and the arm base 50 in each of the aforementioned first and second embodiments, the present disclosure is not limited to this. For example, the medical manipulator 1 may not include the medical cart 3, the positioner 40, or the arm base 50, but may include only the manipulator arms 60.

The functionality of the elements disclosed herein may be implemented using circuitry or processing circuitry that includes general purpose processors, special purpose processors, integrated circuits, application specific integrated circuits (ASICs), conventional circuitry and/or combinations thereof that are configured or programmed to perform the disclosed functionality. Processors are considered processing circuitry or circuitry as they include transistors and other circuitry therein. In the present disclosure, the circuitry, units, or means are hardware that carries out or is programmed to perform the recited functionality. The hardware may be hardware disclosed herein or other known hardware that is programmed or configured to carry out the recited functionality. When the hardware is a processor that may be considered a type of circuitry, the circuitry, means, or units are a combination of hardware and software, and the software is used to configure the hardware and/or processor.

What is claimed is:

1. A robotic surgical system comprising:
    a manipulator arm having a tip end to which a surgical instrument is attached;
    a pivot position setter comprising pivot buttons to set a pivot position that serves as a fulcrum for movement of the surgical instrument attached to the manipulator arm;
    a storage comprising a memory; and
    a controller; wherein
    the controller is configured or programmed to perform operations comprising operations to:
        set a temporary pivot position based on an operation on the pivot position setter;
        adjust a position by a predetermined length from the temporary pivot position; and
        store the position adjusted by the predetermined length as the pivot position in the storage.

2. The robotic surgical system according to claim 1, wherein the controller is configured or programmed to perform operations comprising operations to:
    adjust the position by the predetermined length along a direction in which the surgical instrument extends from the temporary pivot position; and
    store the position adjusted by the predetermined length as the pivot position in the storage.

3. The robotic surgical system according to claim 1, further comprising:
    an input device comprising a touch panel for inputting the predetermined length in advance; wherein
    the controller is configured or programmed to perform operations comprising operations to store a position adjusted by the predetermined length input in advance from the temporary pivot position as the pivot position in the storage.

4. The robotic surgical system according to claim 3, further comprising:
    a remote control apparatus including an operation handle to operate the surgical instrument; wherein
    the input device is arranged on the remote control apparatus.

5. The robotic surgical system according to claim 1, wherein the controller is configured or programmed to perform operations further comprising operations to:
    calculate a thickness of an abdominal wall of a patient based on a three-dimensional model created from an image of the patient captured in advance; and
    store a position adjusted by a length corresponding to ½ of the thickness from the temporary pivot position as the pivot position in the storage.

6. The robotic surgical system according to claim 1, wherein the controller is configured or programmed to perform operations comprising operations to:
    set the temporary pivot position where a tip end of the surgical instrument attached to the tip end of the manipulator arm is located at a position corresponding to an insertion position of a trocar inserted into a body surface of a patient and the pivot position setter is operated;
    set a second temporary pivot position where the tip end of the surgical instrument is located at a position corresponding to the tip end of the trocar located inside a body of the patient and the pivot position setter is operated; and
    store a position adjusted based on the first temporary pivot position and the second temporary pivot position as the pivot position in the storage.

7. The robotic surgical system according to claim 6, wherein the controller is configured or programmed to perform operations comprising operations to
    calculate a difference value by subtracting an amount of protrusion of the tip end of the trocar from an abdominal wall of the patient to an inside of the body of the patient from a distance between the first temporary pivot position and the second temporary pivot position; and
    store a position moved by ½ of the difference value from the first temporary pivot position to the inside of the body of the patient as the pivot position in the storage.

8. The robotic surgical system according to claim 1, further comprising:
    a second manipulator arm having a tip end to which a surgical instrument is attached; and
    a second pivot position setter comprising second pivot buttons to set a second pivot position that serves as a fulcrum for movement of the surgical instrument attached to the second manipulator arm; wherein
    the controller is configured or programmed to perform operations comprising operations to:
        set a second temporary pivot position based on an operation on the second pivot position setter; and
        store a position adjusted by a predetermined length from the second temporary pivot position as the second pivot position in the storage.

9. The robotic surgical system according to claim 1, further comprising:
    a receiver comprising a touch panel configured to receive a change in the pivot position; wherein
    the controller is configured or programmed to perform operations comprising operations to store the changed and received pivot position in the storage in response to the receiver receiving the change in the pivot position after the pivot position is stored in the storage.

10. The robotic surgical system according to claim 9, wherein
    the receiver receives an amount of change from the pivot position; and the controller is configured or programmed to perform operations comprising operations to store a position moved by the amount of change along a direction in which the surgical instrument extends as the changed pivot position in the storage.

11. The robotic surgical system according to claim 1, wherein the controller is configured or programmed to perform operations comprising operations to store a position adjusted by the predetermined length from the temporary pivot position such that the pivot position is located at a central portion of an abdominal wall of a patient in a thickness direction as the pivot position in the storage.

12. A method for setting a pivot position, the method comprising:
receiving an operation on a pivot position setter comprising pivot buttons to set a pivot position that serves as a fulcrum for movement of a surgical instrument attached to a tip end of a manipulator arm;
setting a temporary pivot position based on the operation on the pivot position setter;
adjusting a position by a predetermined length from the set temporary pivot position; and
storing the position adjusted by the predetermined length as the pivot position in a storage.

13. The method for setting the pivot position according to claim 12, wherein
the adjusting comprises adjusting the position by the predetermined length along a direction in which the surgical instrument extends from the set temporary pivot position, and
the storing of the position adjusted by the predetermined length as the pivot position in the storage includes storing the position adjusted by the predetermined length along the direction in which the surgical instrument extends from the temporary pivot position as the pivot position in the storage.

14. The method for setting the pivot position according to claim 12, wherein the storing of the position adjusted by the predetermined length as the pivot position in the storage includes storing a position adjusted by the predetermined length input in advance through an input device from the temporary pivot position as the pivot position in the storage.

15. The method for setting the pivot position according to claim 14, further comprising:
a remote control apparatus including an operation handle to operate the surgical instrument; wherein
the input device comprises a touch panel arranged on the remote control apparatus.

16. The method for setting the pivot position according to claim 12, wherein the storing of the position adjusted by the predetermined length as the pivot position in the storage includes:
calculating a thickness of an abdominal wall of a patient based on a three-dimensional model created from an image of the patient captured in advance; and
storing a position adjusted by a length corresponding to ½ of the thickness from the temporary pivot position as the pivot position in the storage.

17. The method for setting the pivot position according to claim 12, wherein
the setting of the temporary pivot position based on the operation on the pivot position setter includes:
setting the temporary pivot position where a tip end of the surgical instrument attached to the tip end of the manipulator arm is located at a position corresponding to an insertion position of a trocar inserted into a body surface of a patient and the pivot position setter is operated; and
setting a second temporary pivot position where the tip end of the surgical instrument is located at a position corresponding to the tip end of the trocar located inside a body of the patient and the pivot position setter is operated; and
the storing of the position adjusted by the predetermined length as the pivot position in the storage includes storing a position adjusted based on the first temporary pivot position and the second temporary pivot position as the pivot position in the storage.

18. The method for setting the pivot position according to claim 17, wherein the storing of the position adjusted by the predetermined length as the pivot position in the storage includes:
calculating a difference value by subtracting an amount of protrusion of the tip end of the trocar from an abdominal wall of the patient to an inside of the body of the patient from a distance between the first temporary pivot position and the second temporary pivot position; and
storing a position moved by ½ of the difference value from the first temporary pivot position to the inside of the body of the patient as the pivot position in the storage.

19. The method for setting the pivot position according to claim 12, further comprising:
a second manipulator arm having a tip end to which a surgical instrument is attached; and
a second pivot position setter comprising second pivot buttons to set a second pivot position that serves as a fulcrum for movement of the surgical instrument attached to the second manipulator arm; wherein
the method further comprises:
setting a second temporary pivot position based on an operation on the second pivot position setter; and
storing a position adjusted by a predetermined length from the set second temporary pivot position as the second pivot position in the storage.

20. The method for setting the pivot position according to claim 12, wherein the storing of the position adjusted by the predetermined length as the pivot position in the storage includes storing the changed and received pivot position in the storage when a receiver receives a change in the pivot position after the pivot position is stored in the storage.

* * * * *